US005631219A

United States Patent [19]
Rosenthal et al.

[11] Patent Number: 5,631,219
[45] Date of Patent: May 20, 1997

[54] METHOD OF STIMULATING HEMATOPOIESIS WITH HEMOGLOBIN

[75] Inventors: Gary J. Rosenthal, Boulder; Michael J. Gerber, Denver, both of Colo.

[73] Assignee: Somatogen, Inc., Boulder, Colo.

[21] Appl. No.: 208,740

[22] Filed: Mar. 8, 1994

[51] Int. Cl.[6] .......................... A61K 38/16; A01N 61/00;
A01N 1/02; G01N 33/20
[52] U.S. Cl. ..................... 514/6; 514/1; 514/21;
435/2; 435/15; 435/18; 435/69.6; 436/74;
436/63; 436/66; 436/15
[58] Field of Search ........................ 514/6, 2, 21, 1;
435/2, 29, 15, 18, 69.6; 424/529, 85.6;
530/351; 436/74, 63, 66, 15

[56] References Cited

U.S. PATENT DOCUMENTS

| | | | |
|---|---|---|---|
| 4,001,200 | 1/1977 | Bonsen et al. | 260/112.5 R |
| 4,001,401 | 1/1977 | Bonsen et al. | 424/177 |
| 4,053,590 | 10/1977 | Bonsen et al. | 424/177 |
| 4,061,736 | 12/1977 | Morris et al. | 424/177 |
| 4,301,144 | 11/1981 | Iwashita et al. | 424/78 |
| 4,321,259 | 3/1982 | Nicolau et al. | 424/101 |
| 4,336,248 | 6/1982 | Bonhard | 424/101 |
| 4,377,512 | 3/1983 | Ajisaka et al. | 260/112 B |
| 4,401,652 | 8/1983 | Simmonds | 424/101 |
| 4,412,989 | 11/1983 | Iwashita et al. | 424/177 |

(List continued on next page.)

FOREIGN PATENT DOCUMENTS

| | | |
|---|---|---|
| 0132178 | 1/1985 | European Pat. Off. . |
| 0277289 | 8/1988 | European Pat. Off. . |
| 0206448 | 11/1990 | European Pat. Off. . |
| 0231236 | 10/1991 | European Pat. Off. . |
| 0459788 | 12/1991 | European Pat. Off. . |
| 0277289 | 4/1992 | European Pat. Off. . |
| 0361719 | 1/1994 | European Pat. Off. . |
| 8806161 | 8/1988 | WIPO . |
| 8904168 | 5/1989 | WIPO . |
| 8912456 | 12/1989 | WIPO . |
| 9013645 | 11/1990 | WIPO . |
| 9105795 | 5/1991 | WIPO . |
| 9109615 | 7/1991 | WIPO . |
| 9202242 | 2/1992 | WIPO . |
| 9209630 | 6/1992 | WIPO . |
| 9211283 | 7/1992 | WIPO . |
| 9211355 | 7/1992 | WIPO . |
| 9220369 | 11/1992 | WIPO . |
| 9221702 | 12/1992 | WIPO . |
| 9222646 | 12/1992 | WIPO . |
| 9309143 | 5/1993 | WIPO . |
| 9318132 | 9/1993 | WIPO . |
| 9318136 | 9/1993 | WIPO . |
| 9318137 | 9/1993 | WIPO . |

OTHER PUBLICATIONS

"Transfusion", vol. 31, No. 4, 1991, pp 369–371.
Experimental Hematology, vol. 12, pp 587–593, 1984.
New Eng Jour of Medicine, vol. 316, No. 2, 1987, pp 73–78.
Clinical Nephrology, vol. 38, Suppl. No. 1, pp 592–597, 1992.
International Jour of Cell Cloning, vol. 4, pp 432–446, 1986.
Rosenthal, G.J. et al/Stimulation of Hematopoiesis by Recombinant Human Hemoglobin in Human Bone Marrow/Blood/(1994) 84(10), Suppl 1:118a.

(List continued on next page.)

*Primary Examiner*—John Kight
*Assistant Examiner*—Louise Leary
*Attorney, Agent, or Firm*—Marianne F. Novelli; Henry P. Nowak; Theresa A. Brown

[57] ABSTRACT

The present invention relates to a method for stimulating hematopoiesis in a mammal comprising administration of a therapeutically effective amount of a hemoglobin, including recombinant hemoglobin, and methods for treating cytopenias. These cytopenias include anemia, thrombocytopenia, lymphopenia, neutropenia and the like. The stimulation of hematopoiesis can occur both in vivo and ex vivo, as in the treatment of cytopenias associated with disease states, in cell culture or ex vivo expansion of bone marrow cells.

24 Claims, 11 Drawing Sheets

U.S. PATENT DOCUMENTS

| | | | |
|---|---|---|---|
| 4,439,357 | 3/1984 | Bonhard et al. | 260/112 B |
| 4,473,494 | 9/1984 | Tye | 260/112 B |
| 4,473,496 | 9/1984 | Scannon | 260/112 B |
| 4,473,563 | 9/1984 | Nicolau et al. | 424/224 |
| 4,526,715 | 7/1985 | Kothe | 260/112 B |
| 4,529,719 | 7/1985 | Tye | 514/6 |
| 4,584,130 | 4/1986 | Bucci et al. | 260/112 B |
| 4,598,064 | 7/1986 | Walder | 514/6 |
| 4,600,531 | 7/1986 | Walder | 530/385 |
| 4,650,786 | 3/1987 | Wong | 514/6 |
| 4,670,417 | 6/1987 | Iwasaki et al. | 514/6 |
| 4,703,008 | 10/1987 | Lin | 435/240.2 |
| 4,710,488 | 12/1987 | Wong | 514/6 |
| 4,777,244 | 10/1988 | Bonhard et al. | 530/385 |
| 4,810,643 | 3/1989 | Souza | 435/68 |
| 4,826,811 | 5/1989 | Sehgal et al. | 514/6 |
| 4,857,636 | 8/1989 | Hsia | 514/6 |
| 4,861,867 | 8/1989 | Estep | 530/385 |
| 4,868,119 | 9/1989 | Clark et al. | 435/240.2 |
| 4,920,194 | 4/1990 | Feller et al. | 530/385 |
| 4,965,251 | 10/1990 | Stamatoyannopoulos | 514/8 |
| 5,004,681 | 4/1991 | Boyse et al. | 435/2 |
| 5,028,588 | 7/1991 | Hoffman et al. | 514/6 |
| 5,032,396 | 7/1991 | Williams | 424/85.2 |
| 5,032,507 | 7/1991 | Yu et al. | 435/29 |
| 5,032,676 | 7/1991 | Deeley et al. | 530/351 |
| 5,061,620 | 10/1991 | Tsukamoto et al. | 435/7.21 |
| 5,084,558 | 1/1992 | Rausch | 530/385 |
| 5,104,653 | 4/1992 | Michalevicz | 424/85.6 |
| 5,188,828 | 2/1993 | Goldberg et al. | 514/8 |
| 5,198,417 | 3/1993 | Donahue | 514/2 |
| 5,199,942 | 4/1993 | Gillis | 604/4 |
| 5,250,665 | 10/1993 | Kluger et al. | 530/385 |
| 5,264,208 | 11/1993 | Hughes | 424/85.1 |
| 5,296,465 | 3/1994 | Rausch | 514/6 |

OTHER PUBLICATIONS

Feola, M. et al/Clinical Trial of a Hemoglobin Based Blood Substitute in Patients with Sickle Cell Anemia/Surg. GYN. & Obstet./(1992) 174(5):379–386.

Fruttaldo, L. et al./Erythropoietin Treatment of HIV-Related Myelodysplasia/Miner Va Medica/(1993) 84(3):103–105.

Hawkins, W.B. & Johnson, A.C./Bile Pigment and Hemoglobin Interrelation in Anemic Dogs/Am. J. Physiol./(1939)126:326–336.

Ferrari, R./Ricerche Sulla Formazione Della Emoglobina Nella Rana Salata/Archivio Di Scienze Biologiche/Ed. Cappelli/(1932) 17:25–40.

Amberson, W.R./Blood Substitutes/Biol. Res./(1937) 12:48–86.

Furukawa, K./Experimentelle Untersuchungen Zur Chirurgischen Anamiebehandlung Durch Autotransfusion Von Blut/Klin. Wochenschrift/(1992) 1:723–725.

Monette, F.C. & Sigounas, G./Hemin Acts Synergistically With Interleukin–3 to Promote the Growth of Multipotent Stem Cells (CFU–GEMM) in "Serum–Free" Cultures of Normal Murine Bone Marrow/Exp. Hematol./(1988) 16:727–729.

Monette, F.C./The Role of Interleukin–3 and Heme in the Induction of Erythropoiesis/Ann. NY Acad. Sci./(1989) 554:49–58.

Monette, F.C. et al./Specificity of Hemin Action in Vivo at Early Stages of Hematopoietic Cell Differentiation/exp. Hematol./(1984) 12:782–787.

Holden, S.A. et al./Further Characterization of the Hemin–Induced Enhancement of Primitive Erythroid Progenitor Cell Growth in Vitro/Exp. Hematol./(1983) 11(10):953–960.

Porter, P.N. et al./Enhancement of Erythroid Colony Growth in Culture by Hemin/Exp. Hemat./(1979) 7(1):11–16.

Dabney, B.J. & Beaudet, A.L./Increase in Globin Chains and Globin mRNA IN Erythroleukemia Cells in Response to Hemin/Arch. Biochem. & Biophys./(1977) 179:106–112.

Ross, J. & Sautner, D./Induction of Globin mRNA Accumulation by hemin in Cultured Erythroleukemic Cells/ Cell/(1976) 8:513–520.

Feola, M. et al./Nephrotoxicity of Hemoglobin Solutions/Biomat., Art. Cells, Art. Org../(1990) 18(2): 233–249.

Feola, M. et al./Clinical Trial of a Hemoglobin Based Blood Substitute in Patients with Sickel Cell Anemia/Surgery, GYN. & OB./(1992) 174:379–386.

Chertkov, J.L et al./Hematopoietic Effects of Benzene Inhalation Assessed by Murine Long–Term Bone Marrow Culture/J.of Lab. & Clin. Med./(1992) 119(4):412–419.

Abraham, N.G. et al./ Comparison of Hemin Enhancement of Burst–Forming Units–Erythroid Clonal Efficiency by Progenitor Cells From Normal and HIV–Infected Patients/Acta Haem./(1991) 86:189–193.

Cipolleschi, M.G. et al./The Role of Hypoxia in the Maintenance of Hematopoietic Stem Cells/Blood/(1993) 82(7):2031–2037.

Van Zant, G./Studies of Hematopoietic Stem Cells Spared by 5–Fluorouracil/J. Exp. Med./(1984) 159:679–690.

Abraham, N.G. et al./Microenvironmental Toxicity of Azidothymidine: Partial Sparing With Hemin/Blood/(1989) 74(1):139–144.

Reincke, U. et al./Adherent Stem Cells: Frequency in Mouse Marrow and Terminal Clone Sizes in Long–Term Culture/Exp. Hematol./(1985) 13:545–553.

QuesenBerry, P.J./The Concept of the Hemopoietic Stem Cell—Hemopoietic Stem Cells, Progenitor Cells, and Growth Factors/Hematology/(1990) 129–147/Ed: W.J. Williams; E. Beutler; A.J. Erslev; M.A. Lichtman.

Grutzmacher, P. et al./Effect of Recombinant Human Erythropoietin on Iron Balance in Maintenance Hemodialysis: Theoretical Considerations, Clinical Experience and Consequences/Clinical Nephrology/(1992) 38 Suppl. 1: S92–S97.

Shuman, M./Hemorrhagic Disorders: Abnormalities of Platelet and Vascular Function—Mechanisms of Hemostasis/Cecil Textbook of Medicine/(1992) 987–999/Ed: J.B. Wyngaarden; L.H. Smith; J.C. Bennett/W.B. Saunders Co/Philadelphia.

Schulz, G.E. & Schirmer, R.H./Principles of Protein Structure/Springer–Verlag/(1979) Table 1–2.

Marotta, C.A. et al./ Human α–Globin Messenger RNA—III. Nucleotide Sequences Derived from Complementary DNA/JBC/(1977) 252: 5040–5053.

Zoller, M.J. & Smith, M./Oligonucleotide–Directed Mutagenesis of DNA Fragments Cloned into M13 Vectors/Methods in Enzymology/(1983) 100:468–500/Academic Press, Inc.

Mertelsmann, R.H. et al./In Vivo Biology and Therapeutic Potential of Hematopoietic Growth Factors and Peripheral Blood Progenitor Cells/Application of Basic Science to Hematopoiesis and the Treatment of Disease/(1993) Ed: E.D. Thomas; S.K. Carter/Raven Press, NY/177–202.

Nicola, N.A./Hematopoietic Growth Factors and Their Receptors–an Overview/Application of Basic Science to Hematopoiesis and the Treatment of Disease/Ed: E.D. Thomas, S.K. Carter/Raven Press, NY/(1993) 51–69.

McCracken, A.A. et al./An Enrichment Selection for Mutants Resulting from Oligonucleotide–Directed Mutagenesis of Double–Stranded DNA/Biotechniques/(1988) 6(4):332–339.

Luisi, B.F. & Nagai, K./Crytsallographic Analysis of Mutant Human Haemoglobins Made in Escherichia Coli/Nature/(1986) 320 555–556.

Creighton, T.E./Proteins Structures and Molecular Principles/(1993) FIG. 3–9.

Dickerson, R.E. & Geis, I./Hemoglobin: Structure, Function, Evolution, and Pathology/(1983) Chapter 3/Benjamin/Cummings Publishing Company, Inc.

Liebhaber, S.A. et al./Cloning and Complete Nucleotide Sequence of Human 5'–α–Globin Globin Gene/PNAS USA/(1980) 77(12):7054–7058.

Huang, C.M. et al./ Nutritional Status of Patients With Acquired Immunodeficiency Syndrome/Clin. Chem./(1988) 34(10):1957–1959.

Rabiner, S.F. et al./Evaluation of a Stroma–Free Hemoglobin Solution For use as a Plasma Expander/J. Exp. Med./(1967) 126:1127–1142.

Sunder–Plassmann, L. et al./Stromafree Haemoglobin Solution as a Blood Replacement Fluid Actual State and Problems/Europ. J. Intensive Care Med./(1975) 1:37–42.

Devenuto, F. et al/Appraisal of Hemoglobin Solution as a Blood Substitute/Surgery, Gynecology & Obstetrics/(1979) 149:417–436.

Amberson, W.R. et al/Clinical Experience With Hemoglobin–Saline Solutions/J. of Applied Phys. (1949) 1(7):469–489.

Kaplan, M.E./Acquired Hemolytic Disorders/Cecil Textbook of Medicine/Ed: J.B. Wyngaarden; Smith, L.H.; Bennett, J.C./W.B. Saunders Co Publishing/Philadelphia/(1992) 865–872.

Naswitis, K./Ueber Auslosung Von Zellvermehrungen Durch Wundhormone Bei Hoheren Saugetieren Und Dem Menschen/DTSCH. Med. Wochenschrift/(1922) 48:187–188.

Hooper, C.W. et al/Blood Regeneration Following Simple Anemia—V. The Influence of Blaud's Pills and Hemoglobin/AM J. of Phys./(1920) 53(2) 263–282.

Nathan, D.G./Hematologic Diseases—Introduction to Hematologic Diseases/Cecil Textbook of Medicine/Ed. J.B. Wyngaarden; L.H. Smith; J.C. Bennett/W.B. Saunders Co/Philadelphia/(1992) 817–836.

Bagby, G.C./Leukopenia/Cecil Textbook of Medicine/J.B. Wyngaarden; L.H. Smith; J.C. Bennett/W.B. Saunders Co/Philadelphia/(1992) 907–914.

Erslev, A.J./Erythrokinetics—Production of Erythrocytes/hematology/Ed. W.J. Williams; McGraw–Hill, Inc. Publishing/New York/(1990) 389–407.

Bagby, G.C./Leukocytosis and Leukemoid Reactions/Cecil Textbook of Medicine/Ed: J.B. Wyngaarden; L.H. Smith; J.C. Bennett/W.B. Saunders Co/Philadelphia/(1992) 914–920.

Nagai, K. et al/Distal Residues in the Oxygen Binding Site of Haemoglobin Studied by Protein Engineering/Nature/(1987) 329:858–860.

Lindenbaum, J./An Approach to the Anemias/Cecil Textbook of Medicine/Ed: J.B. Wyngaarden; L.H. Smith; J.C. Bennett/W.B. Saunders Co/Philadelphia/(1992) 822–831.

Winslow, W.M./Hemoglobin–Based Red Cell Substitutes/The Jons Hopkins Univ. Press/Baltimore/(1992) Entire Text.

METHOD OF STIMULATING HEMATOPOIESIS WITH HEMOGLOBIN

FIELD OF INVENTION

The present invention relates to a novel method of stimulating hematopoiesis by administration of a suitable amount of hemoglobin.

BACKGROUND OF THE INVENTION

Hematopoiesis is the process of blood cell production which takes place in the bone marrow. Stem cells in the bone marrow are the progenitor cells for all of the various cell types found in the circulating blood. These stem cells are functionally defined by their capacity to repopulate, on a long-term basis, all of the hematopoietic cell lineages in a lethally irradiated animal [Nicola, N. A. (1993) in *Application of Basic Science to Hematopoiesis and the Treatment of Disease*, E. D. Thomas and S. K. Carter (ed), Raven Press, New York]. Through a complex series of regulatory events, stem cells differentiate into a number of types of cells including at least red blood cells, leukocytes, lymphocytes, platelets (thrombocytes), monocytes, macrophages, mast cells, basophils, eosinophils, β-lymphocytes and T-lymphocytes. Millions of each type of new blood cells are produced daily and are released into the circulating blood to replace destroyed blood cells and maintain homeostasis. (Nathan, D. G. (1992) in *Cecil Textbook of Medicine*, L. B. Wyngaarden, L. H. Smith and J. C. Bennett, ed., W. B. Saunders Co, Philadelphia, pages 817–836).

The production of the different cell types can be modulated in response to exogenous stimuli such as infection or blood loss. For example, during infection white blood cells (leukocytes) are mobilized from peripheral stores, e.g. along the margins of vascular walls (the so-called process of de-marginalization) and there is a concomitant increase of leukocyte production in the bone marrow (Bagby, G. C. (1992) in *Cecil Textbook of Medicine*, J. B. Wyngaarden, L. H. Smith and J. C. Bennett, ed., W. B. Saunders Co., Philadelphia, pages 914–920). Acute blood losses such as menstruation, trauma or surgical blood loss may result in anemia wherein the blood is deficient in red blood cells, in hemoglobin or in total volume (hematocrit<40%, hemoglobin<12 grams/dl, red blood cells<4×10$^6$/ul, or mean cell volume<80 fl; Nathan, D. G. (1992) in *Cecil Textbook of Medicine*, J. B. Wyngaarden, L. H. Smith and J. C. Bennett, ed., W. B. Saunders Co., Philadelphia, pages 817–836). The red cell mass (total red blood cells, either total number, weight or volume) acts as an organ that delivers oxygen to tissues. Red cell mass and the rate of red blood cell production are closely coupled to the supply and demand for oxygen in body tissues. Red blood cell production is stimulated by low tissue tension of oxygen. Anemic conditions result in reduced oxygen levels in tissues (hypoxia). Hypoxia in the kidney is sensed by the renal parenchyma which stimulates the release of erythropoietin from the kidney. Erythropoietin is the major regulatory hormone of erythropoiesis produced in response to hypoxia resulting from alterations in the red cell mass. (Erslev, A. J. (1990) in *Hematology*, W. J. Williams, E. Beutler, A. J. Erslev and M. A. Lichtman eds, McGraw-Hill, Inc. New York, pp 389–407).

Other deficits in specific circulating cell types may occur as well. Leukopenia, a general term that describes decreases in any one of a number of different leukocyte cell populations, may result from a de-coupling of the process of demargination and the rate of replacement of cells differentiated from progenitor bone marrow cell lines (Bagby, G. C. (1992) in *Cecil Textbook of Medicine*, J. B. Wyngaarden, L. H. Smith and J. C. Bennett, ed. W. B. Saunders Co., Philadelphia, pages 914–920). Neutropenia, a decrease in circulating neutrophils to <2×10$^9$ cells per liter, results in a greatly increased risk of severe bacterial infection (Kaplan, M. E. (1992) in *Cecil Textbook of Medicine*, J. B. Wyngaarden, L. H. Smith and J. C. Bennett, ed. W. B. Saunders Co, Philadelphia, pages 907–914). Thrombocytopenias are defined as decreases in circulating platelet levels to approximately <100,000/μL (Shuman, M. (1992) in *Cecil Textbook of Medicine*, J. B. Wyngaarden, L. H. Smith and J. C. Bennett, ed. W. B. Saunders Co, Philadelphia, pages 987–999). Low circulating thrombocytes may be the result of a number of underlying conditions such as bone marrow injury, the utilization of chemotoxic agents, suppression of the bone marrow due to chemotherapeutic or radiotherapeutic agents, heavy metal poisoning, hemolytic uremic syndrome, HIV infection, tuberculosis, aplastic anemia, thrombotic thrombocytopenic purpura, and immune disorders such as idiopathic thrombocytopenic purpura, leukemias, and myelofibrosis. These thrombocytopenias can result in life-threatening uncontrolled bleeding (Shuman, M. (1992) in *Cecil Textbook of Medicine*, J. B. Wyngaarden, L. H. Smith and J. C. Bennett, ed. W. B. Saunders Co, Philadelphia, pages 987–999).

Each of these disturbances in hematopoiesis may result in an upregulation of the bone marrow differentiation processes which re-supplies the deficient cell population. However, some disturbances in hematopoiesis are so severe that therapeutic intervention is required.

The broad range of cytopenias (decreases in the circulating population of any given blood cell type) can be treated with only a limited number of therapeutic modalities. For example, management of neutropenia is generally limited to treatment of the underlying disease state that results in neutropenia. Such diseases include Felty's syndrome, myelodysplasia, hypersplenism, some cancers, and bone marrow compromises resulting from, for example, toxic chemotherapeutic drugs or toxins. There are few treatments specifically designed to increase neutrophil levels in the blood. These treatments include:

(1) lithium carbonate treatment, although this has been found to have significant toxicity (2) immunosuppressive therapy, typically reserved for treatment of patients whose neutropenia is the result of an autoimmunologically mediated destruction of neutrophils (3) bone marrow transplantation, which, although effective if successful, is associated with significant mortality, and (4) neutrophil transfusion, which can be costly and is ineffective unless maintained for a significant period of time due to the very short half life of neutrophils in the blood stream (Kaplan, M. E. (1992) in *Cecil Textbook of Medicine*, J. B. Wyngaarden, L. H. Smith and J. C. Bennett, ed. W. B. Saunders Co, Philadelphia, pages 907–914).

Treatment for thrombocytopenia is typically an infusion of platelets. Platelet infusions, as with infusions from any human derived blood product, carry significant risk for transmission of infective agents. Moreover, repeated transfusions of platelets may cause the formation of multiple alloantibodies which result in not only the destruction of the transfused platelets but also the destruction of the patient's endogenous thrombocyte population.

Anemias can be resolved by treating the underlying cause of the anemia, such as renal failure, liver disease, endocrine disorders, parvovirus, Epstein-Barr virus, or hepatitis C virus. However, the direct formation of red blood cells can be stimulated with a limited number of therapeutics. Treatments include administration of iron, hemin (a source of iron) or erythropoietin, a naturally occurring or recombinantly produced hematopoietic growth factor. The efficacy of iron or hemin therapy is limited due to poor bioavailability of the iron in these compounds as well as toxicity of the high dosages required to enhance erythropoiesis. In addition, iron therapy is not useful for anemias that are not due to simple iron deficiency. Erythropoietin therapy is limited because it does not appear to be effective in mobilizing endogenous iron stores and only enhances production of erythroid progenitor cells. Without mobilization of these iron stores, erythropoiesis cannot be sustained. For example, regular administration of recombinant erythropoietin to dialysis patients with chronic renal failure-induced anemia results in sustained erythropoiesis and an increase in hematocrit. However, continued erythropoiesis in this situation frequently results in iron deficiency that can limit the long term effectiveness of this treatment modality (Grützmacher, P. (1992) Clin. Nephrol., 38: S92–S97).

The most promising therapeutic modalities for treatment of a number of cytopenias center on the administration of hematopoietic growth factors. Neutropenia has been treated with administration of with GM-CSF or G-CSF (granulocyte-macrophage colony stimulating factor and granulocyte stimulating factor, respectively). As discussed above, anemia in chronic renal failure has been treated with erythropoietin.

However, the hematopoietic system is complex; sustained, enhanced hematopoiesis is a complex interaction between growth factors, inhibitors and receptors. To date, at least twenty growth factors have been recognized (Nicola, N. A. (1993) in *Application of Basic Science to Hematopoiesis and the Treatment of Disease*, E. D. Thomas and S. K. Carter (ed), Raven Press, New York). These include Granulocyte-Macrophage Colony Stimulating Factor (GM-CSF), Macrophage Colony-Stimulating Factor (M-CSF), Granulocyte Colony-Stimulating Factor (G-CSF), Stem Cell Factor (SCF), Erythropoietin (EPO) and Interleukins 1–13 (IL1 to IL7) [Quesenberry, P. J. (1990) in *Hematology*, W. J. Williams, E. Beutler, A. J. Erslev and M. A. Lichtman (eds), McGraw-Hill, Inc. New York, pp 129–147; Nicola, N. A. (1993) in *Application of Basic Science to Hematopoiesis and the Treatment of Disease*, E. D. Thomas and S. K. Carter (ed), Raven Press, New York).

A number of these growth factors have been cloned and expressed recombinantly. These include G-CSF (Souza, L. M., U.S. Pat. No. 4,810,643), M-CSF (Clark, S. C. and Wong, G. G., U.S. Pat. No. 4,868,119), IL-3 (Biasdale, J. H. C., EP 355093), erythropoietin (Lin, U.S. Pat. No. 4,703,008), stem cell factor (Zsebo, K. M. et al., PCT/US90/05548), and GM-CSF (Deeley M., et al., U.S. Pat. No. 5,023,676). Administration of these alone or in combination have resulted in significant hematopoiesis both in vitro and in vivo (Mertelsmann, R. H. (1993) in *Application of Basic Science to Hematopoiesis and the Treatment of Disease*, E. D. Thomas and S. K. Carter (ed), Raven Press, New York; Williams, U.S. Pat. No. 5,032,396; Zsebo et al., PCT/US90/05548; Gillis, S. U.S. Pat. No. 5,199,942; Donahue, R. E., U.S. Pat. No. 5,198,417). Of these growth factors, erythropoietin is unusual in that it acts as a hematopoietic regulator which is selective for one cell lineage, the red blood cell lineage. Most hematopoietic growth factors are not specific and affect, to a different extent, multiple hematopoietic cell lines. Most hematopoietic growth factors are produced at multiple sites in the body, and many act locally and are rarely found in circulation (Nicola, N. A. (1993) in *Application of Basic Science to Hematopoiesis and the Treatment of Disease*, E. D. Thomas and S. K. Carter (ed), Raven Press, New York). Hematopoietic growth factors are present in extremely small amounts and are difficult to detect except in artificial culture systems and conditioned media. Moreover, hematopoietic growth factors act exclusively to modulate the growth and/or differentiation of the hematopoietic cell lines. The inventors of the present invention have surprisingly found that hemoglobin, whose major function is the transport of oxygen in the body and is found in high concentrations in red blood cells, when purified and administered in low dose, acts as a hematopoietic growth factor.

Early investigators had suggested that there was stimulation of hematopoiesis after administration of cell free hemoglobin (Hooper et al. (1920) Am. J. Physiol. 53: 263–282; Naswitis, K. (1922) Dtsch. med. Wochenschrift 48: 187–188; Furukawa, K. (1922) Klin. Wochenschrift 1: 723–725; Amberson (1937) Biol. Revs. 12: 48–86; Ferrari, R. (1932) Arch. Sci. Biologiche 27: 25–40; Hawkins and Johnson (1939) Am. J. Physiol. 126: 326–336). These investigators suggested that hemoglobin released from lysed red blood cells was the primary hematopoietic factor responsible for the enhancement of erythropoiesis either by direct action on hematopoietic tissues or by furnishing some material required for erythropoiesis, or by both actions (Amberson (1937) Biol. Revs. 12: 48–86 and references therein). Amberson et al. [(1949) J. Appl. Physiol. 1:469–489)] later observed an increase in reticulocyte count and hematocrit (both indicators of erythropoiesis) in 3 of 5 patients after administration of a crude hemoglobin solution. However, administration of the crude hemoglobin utilized in early studies resttlted in renal damage, anaphylaxis, and may have contributed to death (Amberson et al. [(1949) J. Appl. Physiol., 1: 469–489). These toxic effects of hemoglobin administration may have been due to contaminating elements such as stroma or endotoxins in the hemoglobin preparations or to the nature of the hemoglobin itself (DeVenuto et al. (1979) Surg. Gyn. Obstet. 149: 417–436; Sunder-Plassmarm et al. (1975) Europ. J. Intensive Care Med. 1: 3714 42; Feola, et al. (1990) Biomat. Art. Cell, Art. Org. 18:233–249). The untreated human hemoglobin tetraruer is composed of two $\alpha$ subunits and two $\beta$ subunits. The tetramer, if outside a red blood cell, will dissociate into two $\alpha/\beta$ dimers which can pass into the kidney and can cause renal failure at higher doses. Any uncrosslinked hemoglobin, when administered even in low doses is cleared from the body extremely rapidly, on the order of minutes. Stroma from poorly purified red blood cell preparations resulted in anaphylaxis. Thus, even though there was some evidence that hemoglobin administration might result in erythropoiesis, no hemoglobin solution existed which could be administered safely and effectively.

The enhancement of erythropoiesis upon the administration of crude hemoglobin solutions is consistent with the observation that anemia due to hemolysis is associated with a more pronounced erythroid hyperplasia and reticulocytosis than blood loss anemia of the same magnitude (Erslev, A. J. (1990) in *Hematology*, W. J. Williams, E. Beutler, A. J. Erslev and M. A. Lichtman (eds), McGraw-Hill, Inc. New York, pp 389–407).

In the late 1970's, work in multiple labs demonstrated that treatment of mouse erythroleukemia cells and normal bone marrow cells with hemin increased the synthesis of hemoglobin at the transcriptional level (Ross, J. and Sautner, D.

(1976) Cell 8: 513; Dabhey, B. J. and Beaudet, A. L. (1977) Arch. Biochem. Biophys. 179: 106; Porter, P. N. et al. (1979) Exp. Hematol. 7: 11). Hemin is the chloride salt of oxidized heme whereas hemoglobin contains reduced heme in the heme pocket of each of the globin subunits. More recently, work by Monette and co-workers has shown that hemin acts synergistically with interleukin 3 to promote the growth of erythroid progenitor cells in vitro and in vivo (in mice). In a series of papers (Holden, S. A. et al. (1983) Exp. Hematol. 11: 953–960; Monette, F. C. et al., (1984) Exp. Hematol. 12: 782–787; Monette, F. C. and Sigounas, G. (1988) Exp. Hematol. 16: 727–729; Monette, F. C. (1989) Ann. New York Acad. Sci. 554: 49–58), Monette clearly demonstrated the capacity of hemin to augment directly and in a cell specific manner the proliferation and/or differentiation of primitive bone marrow erythroid progenitors. Kappas and Abraham have also observed the potentiation of erythroid progenitor cell growth with hemin administration in vitro (PCT publication PCT/US91/05283). However, none of these workers has examined or suggested the role of free hemoglobin in the stimulation of erythropoiesis, nor have any of these investigations suggested that hemoglobin itself may have an erythropoietic effect above and beyond the simple delivery of bioavailable iron.

Indeed, the erythropoietic effect of hemoglobin has been seen only when very large amounts of hemoglobin have been administered. For example, Feola et al. [(1992) Surg. Gyn. Obstet. 174: 379–386] administered high volumes of bovine hemoglobin solution (25% of the patient's total blood volume, approximately 17–35 grams of bovine hemoglobin, or a total of 1.75 g hemoglobin/kg of body weight) to sickle cell children in vaso-occlusive or aplastic crisis. In this group of nine patients who ranged in age from 5–13 years of age, peripheral reticulocytes increased from 3.7±3.9% to 49±6.5% after 3 days and blood hemoglobin increased from 6.34±2.0 gm/dl to 10.6±1.3 gm/dl after 1 week. However, Feola et al. administered antibiotics and antimalarials concurrently with the hemoglobin treatment, and the mediation of the underlying infections alone may have resulted in erythropoiesis. Moreover, administration of such large amounts of any hemoglobin, particularly a non-human derived bovine hemoglobin, may result in unexpected and undesirable immunological effects. Feola et al. state that further examinations are required to determine whether immunologic reactions would develop upon repeated administration of a bovine-derived hemoglobin solution. High dose administration of hemoglobin can serve as simply a source of bioavailable iron, and is thus not significantly different from simple iron treatment of anemia. The inventors of the present invention have surprisingly found that low dose administration of a recombinant hemoglobin results in hematopoiesis as well.

SUMMARY OF THE INVENTION

The present invention relates to a method of stimulating hematopoiesis in a mammal comprising administration of a therapeutically effective amount of hemoglobin. Preferably the therapeutically effective amount of hemoglobin is a low dosage of hemoglobin, preferably <about 1 g of hemoglobin/kg of body weight, more preferably <about 100 mg of hemoglobin/kg of body weight, most preferably <about 10 mg of hemoglobin/kg of body weight.

The invention provides stimulation of hematopoiesis in a mammal by the administration of a pure solution of hemoglobin, preferably derived from recombinant technology, more preferably derived from E. coli expression of a hemoglobin, most preferably containing a mutation, which links the two alpha or two beta or any alpha and any beta subunit of the hemoglobin tetramer.

Another embodiment of the present invention relates to the treatment of a mammal suffering from a cytopenia comprising stimulation of hematopoiesis by the administration of a therapeutically effective amount of hemoglobin.

A further embodiment relates to treatment of a mammal suffering from anemia or an anemia-like condition comprising stimulation of hematopoiesis by the administration of a therapeutically effective amount of hemoglobin.

Another embodiment of the invention comprises administration of a therapeutically effective amount of hemoglobin in combination with other hematopoietic growth factors, including, but not limited to, erythropoietin, interleukins such as IL-3 or IL-11, colony stimulating factors such as G-CSF or GM-CSF, or stem cell factor.

A further embodiment of the invention is the administration of a therapeutically effective amount of hemoglobin, alone or in combination with other hematopoietic growth factors for potentiation of chemotherapeutic or radiotherapeutic treatment modalities.

A further embodiment of the present invention involves the use of hemoglobin as additive to cell culture media used in the ex vivo expansion of progenitor stem cells or blood cells.

A still further embodiment of the present invention involves the use of hemoglobin as an additive to culture media to enhance growth of erythroid progenitor cells.

In a still further embodiment, hemoglobin is used in combination with other hematopoietic factors as an additive to cell culture media to enhance ex vivo expansion of blood components.

In a still further embodiment, hemoglobin is used in combination with other hematopoietic factors as an additive to cell culture media to enhance growth of hematopoietic progenitor cells.

In another embodiment, hemoglobin is used alone or in combination with other growth factors to stimulate hematopoiesis after bone marrow injury.

In a still further embodiment, hemoglobin is used alone or in combination with other growth factors to stimulate erythropoiesis in a mammal suffering from anemia.

Another important embodiment of the present invention is a pharmaceutical composition useful in the method aspects of the present invention comprising therapeutically effective amounts of hemoglobin.

Other features and advantages of the invention will be apparent from the following description of the preferred embodiments thereof and from the claims.

Unless defined otherwise, all technical and scientific terms used herein have the same meaning as commonly understood by one of ordinary skill in the art. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are by way of illustration and not intended as limitation.

"Hematopoiesis," for the purposes of this invention, is a generic term for the process of formation and development of blood cells from progenitor cells as well as formation of progenitor cells of those blood cells. Blood cells include but are not limited to erythrocytes, reticulocytes, monocytes, neutrophils, megakaryotes, eosinophils, basophils, B-cells, macrophages, granulocytes, mast cells, thrombocytes, and leukocytes. Progenitor cells include, but are not limited to burst forming units—erythroid (BFU-E), colony forming units—erythroid (CFU-E), colony forming units—megakaryote (CFU-Meg), colony forming units—granulocyte-macrophage (CFU-GM), colony forming units-macrophage (CFU-M), colony forming units—granulocyte (CFU-G), colony forming units—granulocyte, erythroid, macrophage, megakaryote (CFU-GEMM), colony forming units—monocyte (CFU-M), colony forming units—eosinophil (CFU-Eo), colony forming units—spleen (CFU-S), colony forming units—basophil (CFU-B), pluripotent stem cells, totipotent stem cells, myeloid stem cells, and lymphoid stem cells. "Erythropoiesis" for the purposes of the appended claims is defined as that part of the hematopoietic pathway that leads to the formation of red blood cells. "Thrombopoiesis" for the purposes of the appended claims is defined as that part of the hematopoietic pathway that leads to the formation of thrombocytes. "Leukopoiesis" for the purposes of the appended claims is defined as that part of the hematopoietic pathway that leads to the formation of leukocytes. The process for the formation of other cells of the blood circulation are analogously defined and are distinguished by the use of the suffix "polesis" or "poletic".

For the purposes of the appended claims, a "therapeutically effective amount of hemoglobin" is that amount of naturally derived or recombinantly produced hemoglobin which, when administered to a mammal in need of treatment for deficient blood cells or to a cell culture of blood cells, is sufficient to increase blood cells or progenitor cells. An increase in progenitor cells can be an increase in total number of cells per given volume and for example, in a cell culture such increases can be measured by statistically significant increases in the colony forming unit of interest. On the other hand, in the blood circulation, an increase can mean an increase in the total number of cells, the size of individual cells or, specifically for erythroid cells, the hemoglobin content of individual cells. For example, for erythroid cells, this increase is at least 6% over the baseline level (the size or concentration of the cell type of interest measured prior to treatment), more preferably 10% above the baseline level, still more preferably 20% above the baseline level, most preferably to essentially normal levels in vivo. For in vitro cultures of cells (e.g. ex vivo expansion, cell culture, etc.), an increase can mean an increase in the absolute number of cells, the size of specific cells, or the rate at which cells grow in the culture system. These increases can occur within one day of administration of hemoglobin, but may take up to several months of repeated and/or continued therapeutic administration of hemoglobin. The amounts of hemoglobin that must be administered to enhance hematopoiesis are readily determined by clinicians of ordinary skill in the art and will depend on the underlying cause of the cytopenic condition, the characteristics of the individual patient, mode of administration and the like. Further, a "cytopenic condition" or "cytopenia" is defined as a clinically significant reduction in the numbers, volume, functionality, or distribution of any circulating blood cell type. Cytopenia is intended to embrace at least anemia, thrombocytopenia, neutropenia, and leukopenia.

(1) no treatment, denoted control, (2) oral AZT, denoted AZT, (3) oral AZT and subcutaneous injections of 10 units of EPO three times per week, denoted AZT+EPO (4) oral AZT and intravenous injections of 0.5 mg/kg hemoglobin three times per week, denoted as AZT+0.5 mg/kg Hb, (5) oral AZT and intravenous injections of 1 mg/kg hemoglobin three times per week, denoted as AZT+1 mg/kg Hb, (6) oral AZT, subcutaneous injections of 10 units of EPO three times per week and intravenous injections of 0.5 mg/kg hemoglobin three times per week, denoted as AZT+EPO+0.5 mg/kg Hb, (7) oral AZT, subcutaneous injections of 10 units of EPO three times per week and intravenous injections of 1 mg/kg hemoglobin three times per week, denoted as AZT+EPO+1 mg/kg Hb, AZT was administered to all mice except for controls for five weeks prior to the experiment to ensure adequate AZT effects.

Figure 5:
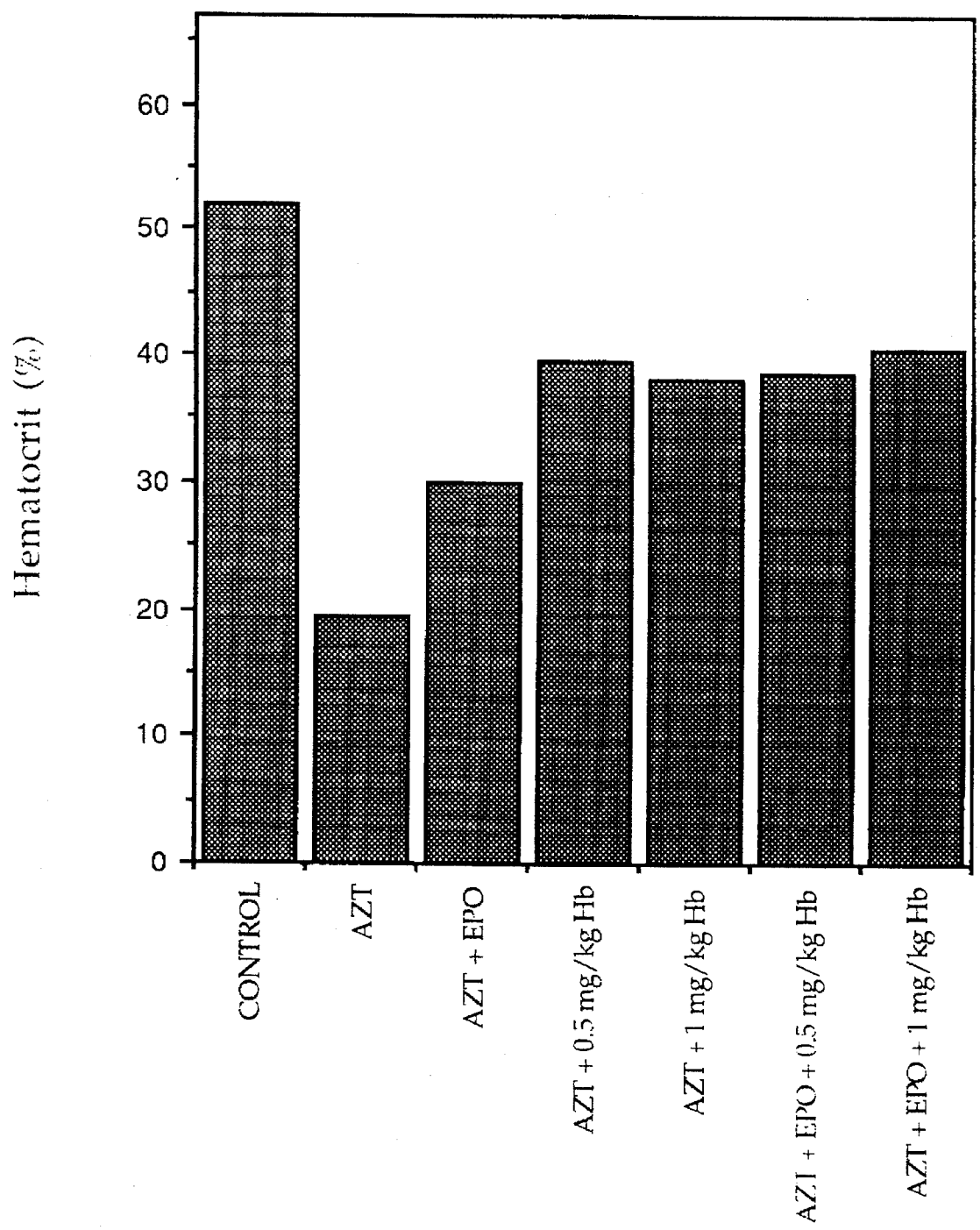

FIG. 5 shows the hematocrit (in percent) of normal BDF1 mice following three weeks of administration of either:

(1) no treatment, denoted control, (2) oral AZT, denoted AZT, (3) oral AZT, and subcutaneous injections of 10 units of EPO three times per week, denoted AZT+EPO (4) oral AZT and intravenous injections of 0.5 mg/kg hemoglobin three times per week, denoted as AZT+0.5 mg/kg Hb, (5) oral AZT and intravenous injections of 1 mg/kg hemoglobin three times per week, denoted as AZT+1 mg/kg Hb, (6) oral AZT, subcutaneous injections of 10 units of EPO three times per week and intravenous injections of 0.5 mg/kg hemoglobin three times per week, denoted as AZT+EPO+0.5 mg/kg Hb, (7) oral AZT, subcutaneous injections of 10 units of EPO three times per week and intravenous injections of 1 mg/kg hemoglobin three times per week, denoted as AZT+EPO+1 mg/kg Hb, AZT was administered to all mice except for controls for five weeks prior to the experiment to ensure adequate AZT effects.

Figure 6:
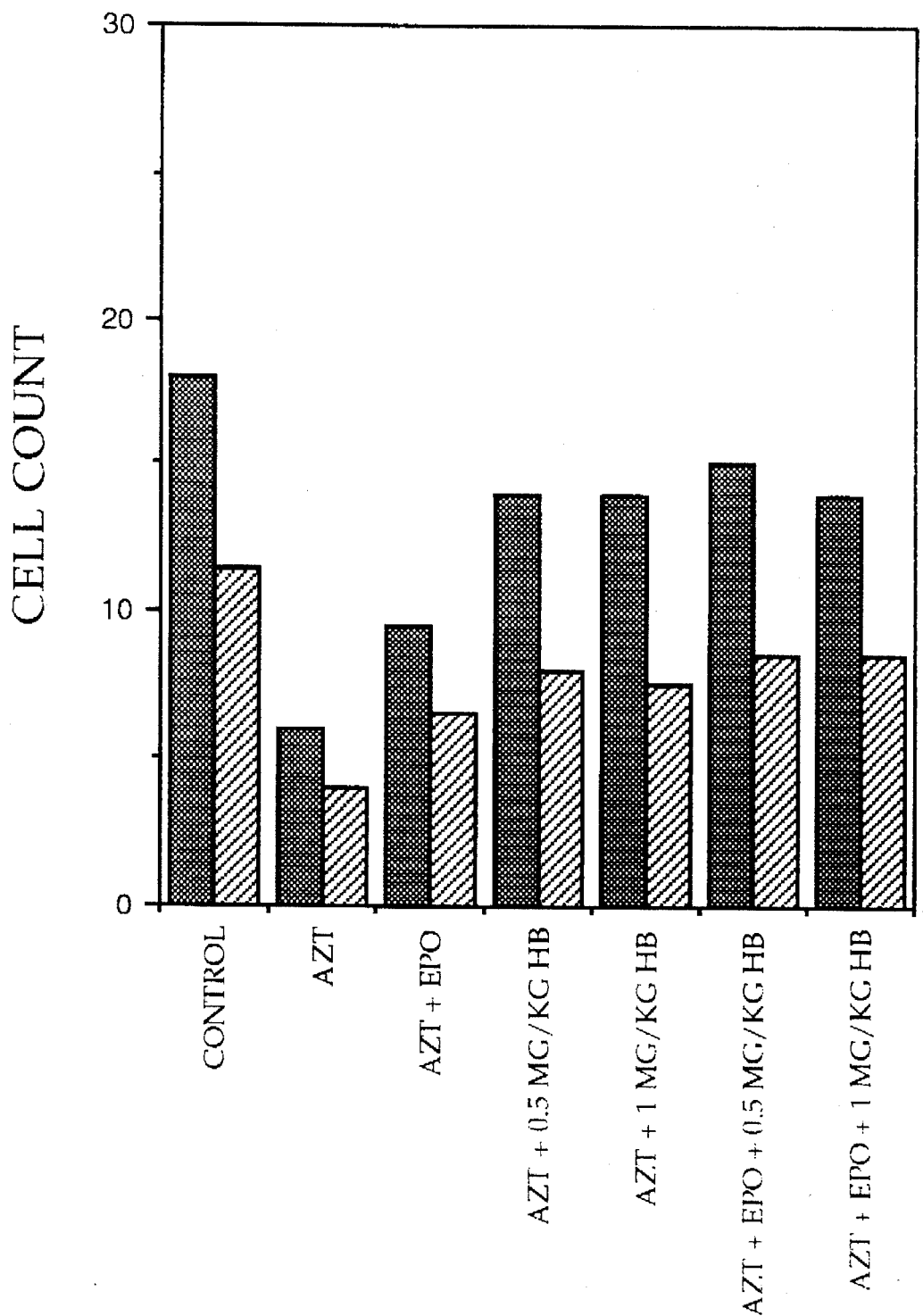

FIG. 6 is a graphical representation of cell counts in normal BDF-1 mice. White blood cell counts are shown as the dark stippled areas, red blood cell counts are shown as the striped areas. Cells were counted following three weeks of administration of either:

(1) no treatment, denoted control on the graph, (2) oral AZT, denoted AZT, (3) oral AZT, and subcutaneous injections of 10 units of EPO three times per week, denoted AZT+EPO (4) oral AZT and intravenous injections of 0.5 mg/kg hemoglobin three times per week, denoted as AZT+0.5 mg/kg Hb, (5) oral AZT and intravenous injections of 1 mg/kg hemoglobin three times per week, denoted as AZT+1 mg/kg Hb, (6) oral AZT, subcutaneous injections of 10 units of EPO three times per week and intravenous injections of 0.5 mg/kg hemoglobin three times per week, denoted as AZT+EPO+0.5 mg/kg Hb, (7) oral AZT, subcutaneous injections of 10 units of EPO three times per week and intravenous injections of 1 mg/kg hemoglobin three times per week, denoted as AZT+EPO+1 mg/kg Hb, AZT was administered to all mice except for controls for five weeks prior to the experiment to ensure adequate AZT effects.

Figure 7:
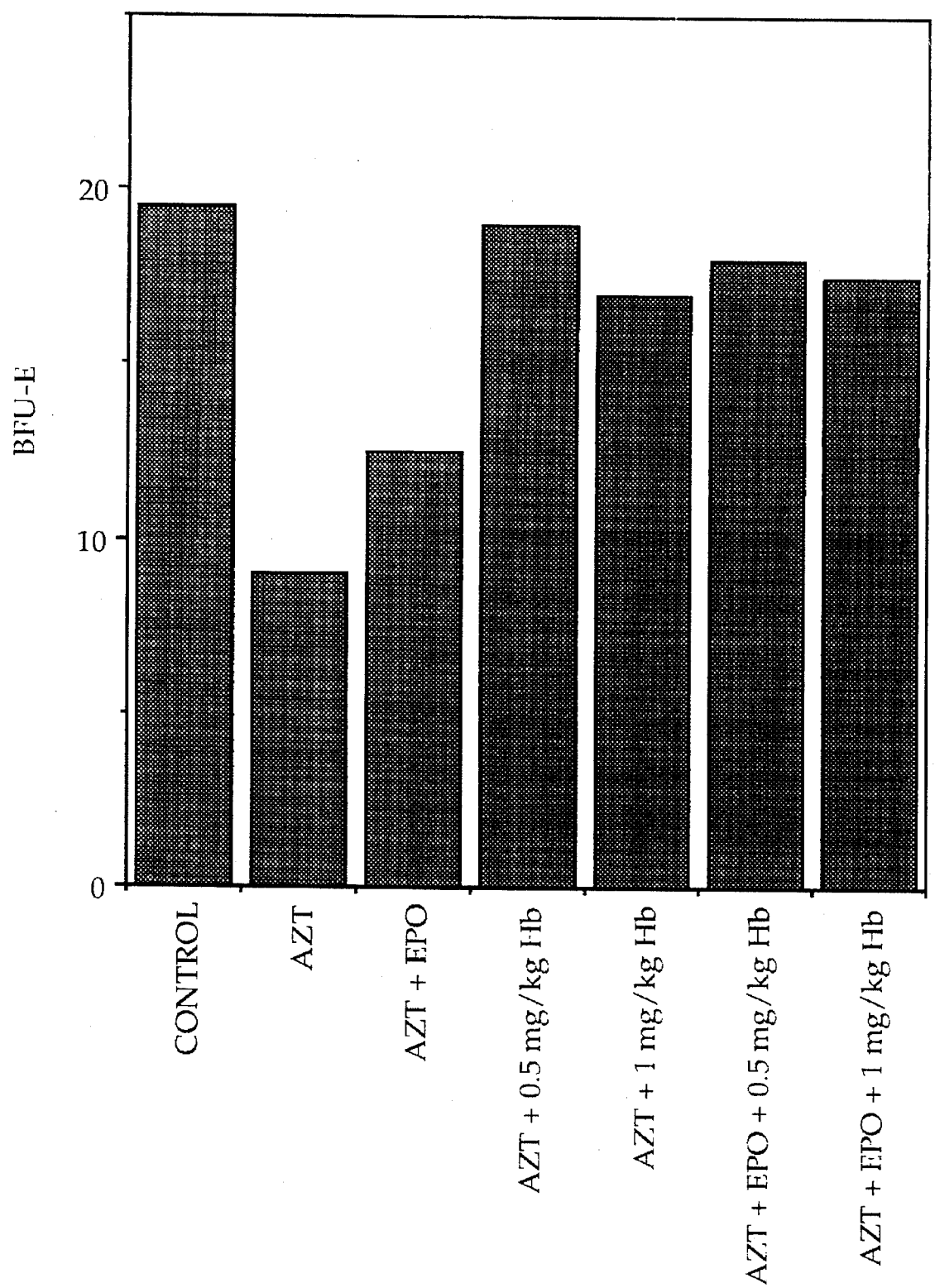

FIG. 7 is a graphical representation of the number of Burst Forming Units—Erythroid (BFU-E) in SCID mice following three weeks of administration of either:

(1) no treatment, denoted control, (2) oral AZT, denoted AZT, denoted AZT+EPO (3) oral AZT and subcutaneous injections of 10 units of EPO three times per week, (4) oral AZT and intravenous injections of 0.5 mg/kg hemoglobin three times per week, denoted as AZT+0.5 mg/kg Hb, (5) oral AZT and intravenous injections of 1 mg/kg hemoglobin three times per week, denoted as AZT+1 mg/kg Hb, (6) oral AZT, subcutaneous injections of 10 units of EPO three times per week and intravenous injections of 0.5 mg/kg hemoglobin three times per week, denoted as AZT+EPO+0.5 mg/kg Hb, (7) oral AZT, subcutaneous injections of 10 units of EPO three times per week and intravenous injections of 1 mg/kg hemoglobin three times per week, denoted as AZT+EPO+1 mg/kg Hb, AZT was administered to all mice except for controls for five weeks prior to the experiment to ensure adequate AZT effects.

Figure 8:
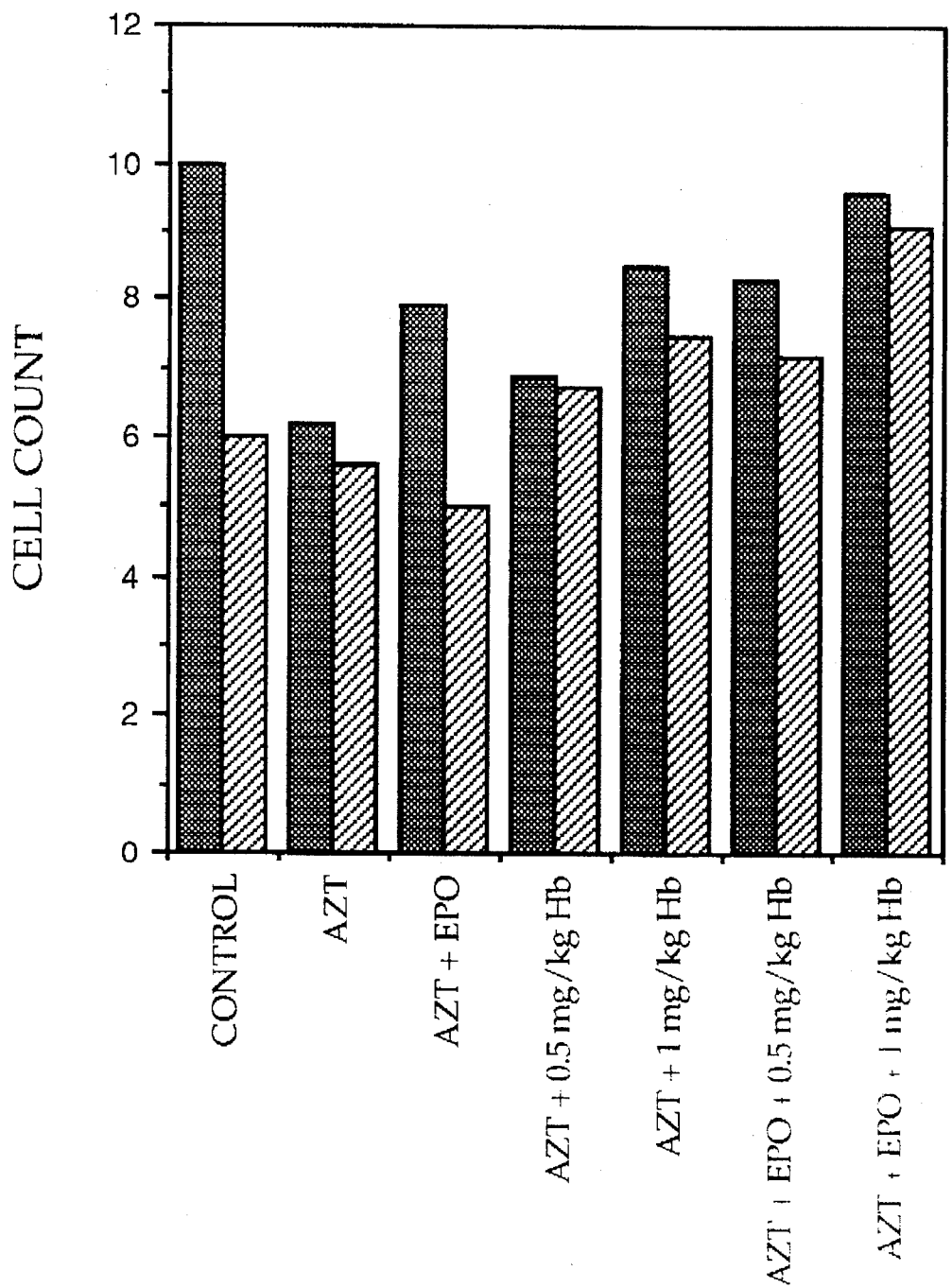

FIG. 8 is a graphical representation of cell counts in Severely Compromised Immunodeficient Disorder (SCID) mice. White blood cell counts are shown as the dark stippled areas, red blood cell counts are shown as the striped areas. Cells were counted following three weeks of administration of either:

(1) no treatment, denoted control on the graph, (2) oral AZT, denoted AZT, (3) oral AZT, and subcutaneous injections of 10 units of EPO three times per week, denoted AZT+EPO (4) oral AZT and intravenous injections of 0.5 mg/kg hemoglobin three times per week, denoted as AZT+0.5 mg/kg Hb, (5) oral AZT and intravenous injections of 1 mg/kg hemoglobin three times per week, denoted as AZT+1 mg/kg Hb, (6) oral AZT, subcutaneous injections of 10 units of EPO three times per week and intravenous injections of 0.5 mg/kg hemoglobin three times per week, denoted as AZT+EPO+0.5 mg/kg Hb, (7) oral AZT, subcutaneous injections of 10 units of EPO three times per week and intravenous injections of 1 mg/kg hemoglobin three times per week, denoted as AZT+EPO+1 mg/kg Hb, AZT was administered to all mice except for controls for five weeks prior to the experiment to ensure adequate AZT effects.

Figure 9:
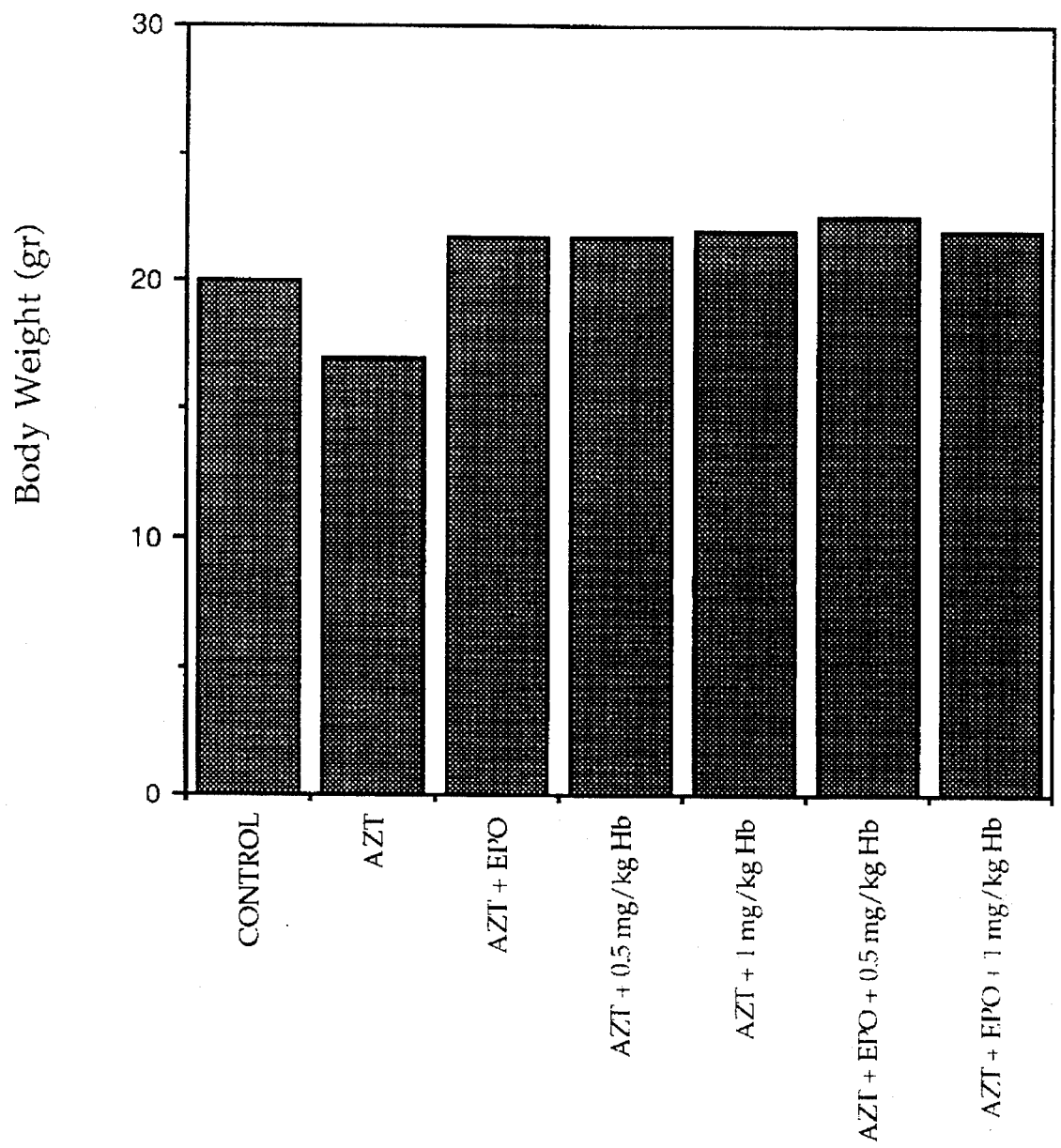

FIG. 9 shows the body weight of normal BDF1 mice following three weeks of administration of either:

(1) no treatment, denoted control, (2) oral AZT, denoted AZT, (3) oral AZT and subcutaneous injections of 10 units of EPO three times per week, denoted AZT+EPO (4) oral AZT and intravenous injections of 0.5 mg/kg hemoglobin three times per week, denoted as AZT+0.5 mg/kg Hb, (5) oral AZT and intravenous injections of 1 mg/kg hemoglobin three times per week, denoted as AZT+1 mg/kg Hb, (6) oral AZT, subcutaneous injections of 10 units of EPO three times per week and intravenous injections of 0.5 mg/kg hemoglobin three times per week, denoted as AZT+EPO+0.5 mg/kg Hb, (7) oral AZT, subcutaneous injections of 10 units of EPO three times per week and intravenous injections of 1 mg/kg hemoglobin three times per week, denoted as AZT+EPO+1 mg/kg Hb, AZT was administered to all mice except for controls for five weeks prior to the experiment to ensure adequate AZT effects.

Figure 10:
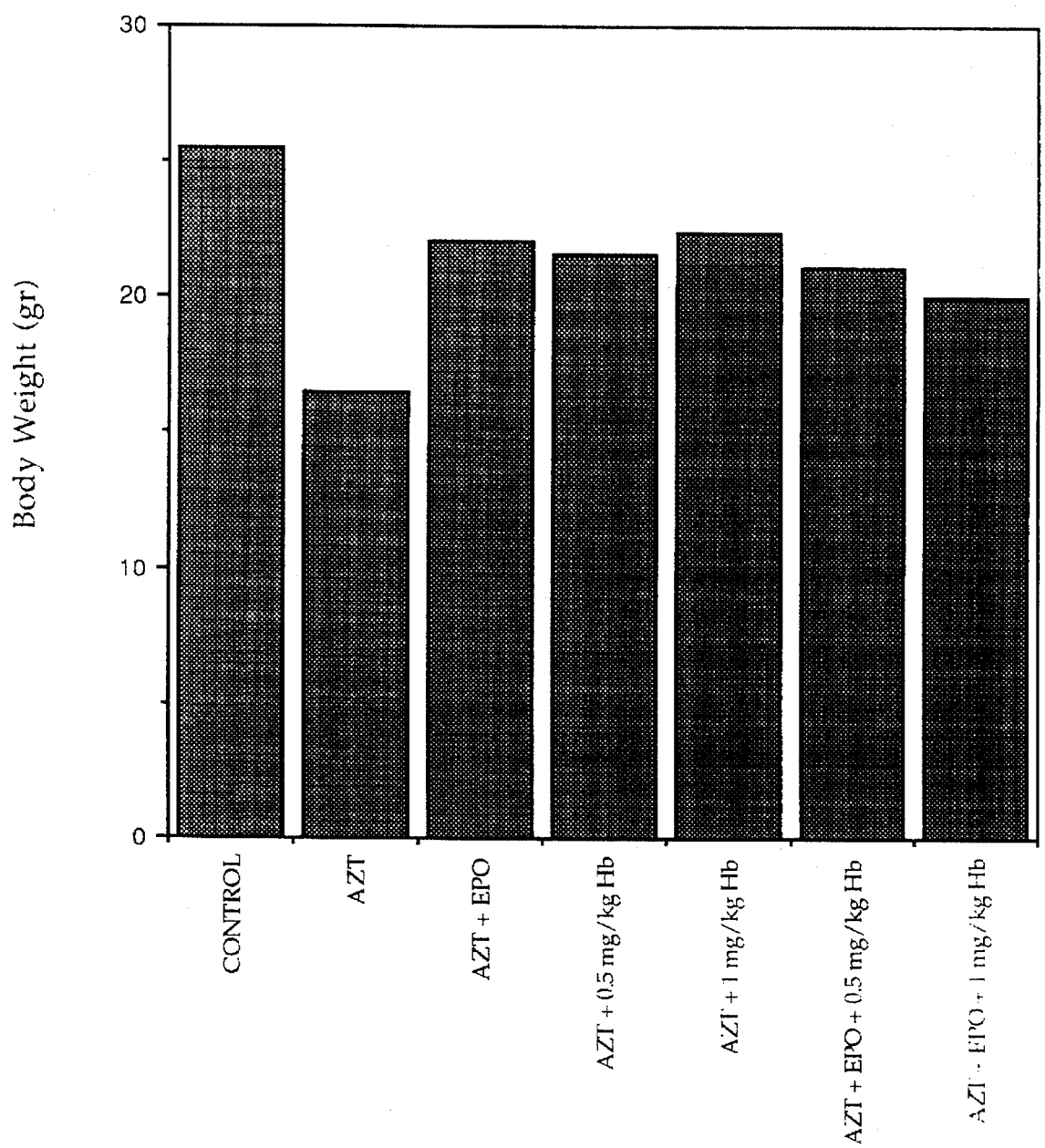

FIG. 10 shows the body weight of SCID mice following three weeks of administration of either:

(1) no treatment, denoted control, (2) oral AZT, denoted AZT, (3) oral AZT and subcutaneous injections of 10 units of EPO three times per week, denoted AZT+EPO (4) oral AZT and intravenous injections of 0.5 mg/kg hemoglobin three times per week, denoted as AZT+0.5 mg/kg Hb, (5) oral AZT and intravenous injections of 1 mg/kg hemoglobin three times per week, denoted as AZT+1 mg/kg Hb, (6) oral AZT, subcutaneous injections of 10 units of EPO three times per week and intravenous injections of 0.5 mg/kg hemoglobin three times per week, denoted as AZT+EPO+0.5 mg/kg Hb, (7) oral AZT, subcutaneous injections of 10 units of EPO three times per week and intravenous injections of 1 mg/kg hemoglobin three times per week, denoted as AZT+EPO+1 mg/kg Hb, AZT was administered to all mice except for controls for five weeks prior to the experiment to ensure adequate AZT effects.

Figure 11:
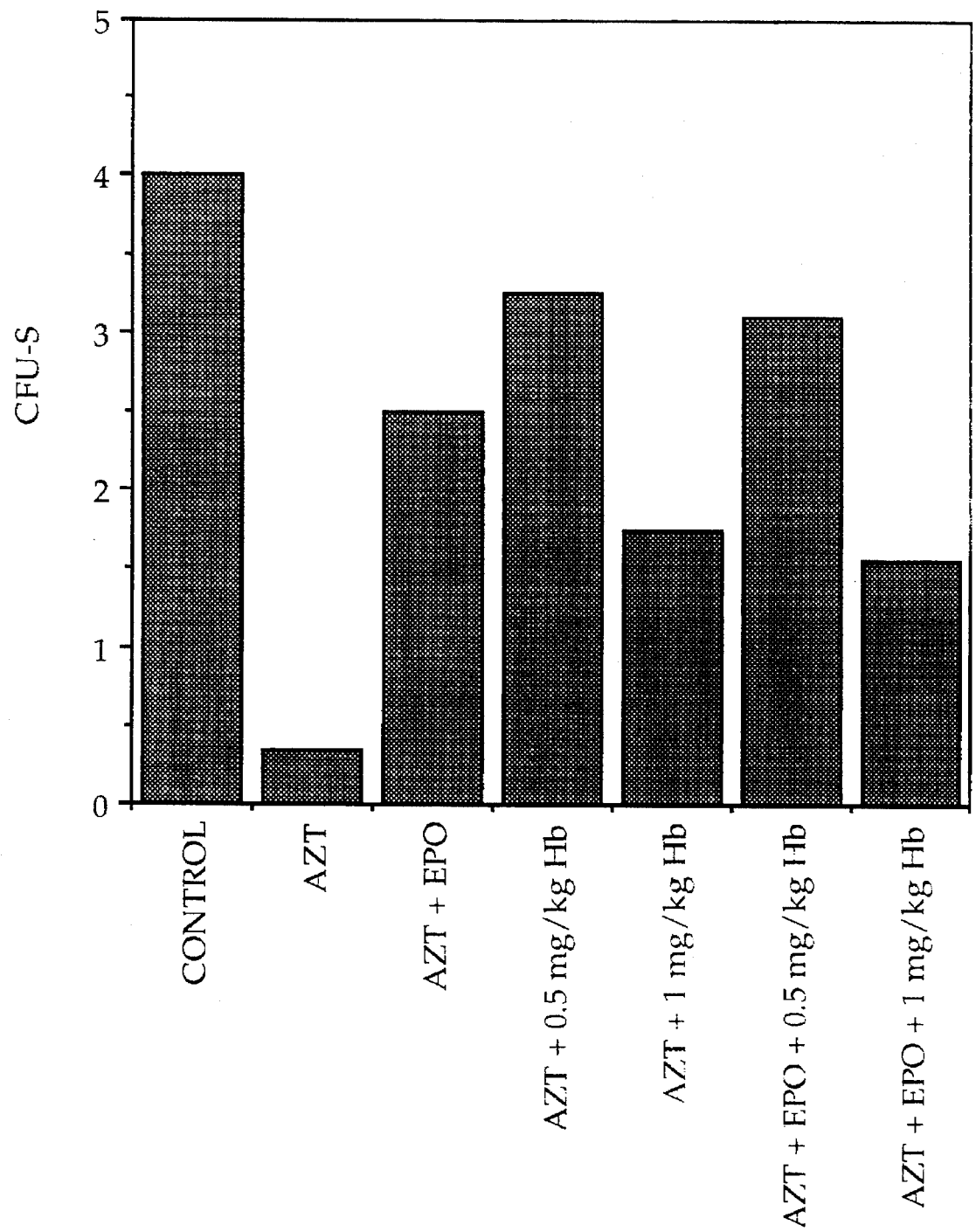

FIG. 11 is a graphical representation of the number of Colony Forming Units—Spleen counted from irradiated mice 8 days after injection of bone marrow collected from BDF1 mice that had been treated for three weeks by intravenous injections of hemoglobin at either 0.5 or 1.0 mg/kg body weight, EPO at 10 Units/mouse, EPO and either 0.5 or 1.0 mg/kg body of hemoglobin or AZT alone prior to harvest of the bone marrow for transplant. AZT was administered to all mice except for controls for five weeks prior to the experiment and during the treatment to ensure adequate effects.

DETAILED DESCRIPTION OF THE INVENTION

The present invention relates to a method of stimulating hematopoiesis in a mammal comprising administration of a therapeutically effective amount of an essentially pure hemoglobin, preferably a recombinantly produced hemoglobin, most preferably a recombinant hemoglobin that does not dissociate into dimers.

Mammalian hemoglobin is generally a tetramer composed of two alpha globin subunits ($\alpha 1$, $\beta 2$) and two beta globin subunits ($\beta_1$, $\beta_2$). There is no sequence difference between $\alpha_1$ and $\alpha_2$ or between $\beta_1$ and $\beta_2$. The subunits are noncovalently associated by Van der Waals forces, hydrogen bonds and, for deoxy Hb (hemoglobin that is not carrying oxygen), salt bridges. Tetrameric hemoglobin is known to dissodate into $\alpha_1\beta_2$ and $\alpha_2\beta_2$ dimers which are eliminated from the bloodstream by renal filtration. This renal filtration of unmodified mammalian hemoglobin dimers can lead to renal failure and death. Hemoglobin dimers can extravasate easily into the tissues and be lost from the circulatory system. Intravascular retention of hemoglobin has been improved by for example, genetic fusion of the subunits of the tetramer as taught by Hoffman, S. J. and Nagai, K. in U.S. Pat. No. 5,028,588, Hoffman, et al., WO 90/13645, and Anderson, D. et al., U.S. patent application Ser. No. 789,179 filed Nov. 8, 1991 or by chemical crosslinking of subunits within a single tetramer or between two or more tetramers (Bonhard, L. and Kothe, N., U.S. Pat. No. 4,777,244; Bonhard, K. and Boysen, U., U.S. Pat. No. 4,336,248; Bonsen, P., et al., U.S. Pat. Nos. 4,001,401, 4,053,590, and 4,001,200; Bucci, E., et al., U.S. Pat. No. 4,584,130; Feller, W., et al., U.S. Pat. No. 4,920,194; Feola, M. et al., PCT publication PCT/US90/07442; Garlick, R. L. et al., PCT publication PCT/US91/07155; Ilan, E. et al., EP publication EP 0361719; Iwasaki, K., et al.; U.S. Pat. No. 4,670,417 and EP Patent EP 0206448; Kluger, R. and Wodzinska, J., PCT publication PCT/CA92/00221 and U.S. Pat. No. 5,250,665; Kothe, N. et al., U.S. Pat. No. 3,525,272; Morris, K. C. et al., U.S. Pat. No. 4,061,736; Pepper, D. S. and McDonald, S. L., EP publication EP 0459788; Scannon, P. J., U.S. Pat. No. 4,473,496; Sehgal, L. R. et al., U.S. Pat. No. 4,826,811; Tye, R. W., U.S. Pat. No. 4,529,719; Walder, J. A. U.S. Pat. Nos. 4,598,064 and 4,600,531 and Ilan, E., EP Patent EP 0361719; among others). In any of these forms, dissociation of hemoglobin into $\alpha_1\beta_1$ and $\alpha_2\beta_2$ dimers is prevented, thus increasing the intravascular retention of the protein and reducing renal toxicity.

Hemoglobin is readily available from a number of natural and recombinant sources. For example, slaughter houses produce very large quantifies of hemoglobin-containing blood which is currently usually sold as an inexpensive fertilizer. Moreover, if particular species or breeds of animals produce a hemoglobin especially suitable for a particular use, those creatures may be specifically bred for this purpose in order to supply the needed blood. Transgenic animals may be produced that can express non-endogenous hemoglobin (Logan, J. S. et at., PCT publication PCT/US92/05000). Human blood can be retrieved from human blood banks that must discard human blood after a certain expiration date.

Hemoglobins derived from natural and recombinant sources have been chemically modified to prevent dissociation and/or improve oxygen carrying characteristics by a variety of techniques. Any of these techniques may be used to prepare hemoglobin. Examples of such modifications are found in Iwashita, Y., et al., U.S. Pat. No. 4,412,989, Iwashita, Y. and Ajisaka, K., U.S. Pat. No. 4,301,144, Iwashita, K., et al., U.S. Pat. No. 4,670,417, Nicolau, Y.-C., U.S. Pat. No. 4,321,259, Nicolau, Y.-C. and Gersonde, K., U.S. Pat. No. 4,473,563, Wong, J. T., U.S. Pat. No. 4,710,488, Wong, J. T. F., U.S. Pat. No. 4,650,786, Bonhard, K., et al., U.S. Pat. No. 4,336,248, Walder, J. A., U.S. Pat. No. 4,598,064, Walder, J. A., U.S. Pat. No. 4,600,531 and Ajisaka, K. and Iwashita, Y., U.S. Pat. No. 4,377,512 among others. Generally, these chemical modifications of hemoglobin involve chemically altering or reacting one or more amino acid residues of the hemoglobin molecule with a reagent that either chemically links the alpha/beta dimers or modifies the steric transformations of the hemoglobin by, for example, binding in the diphosphoglycerate binding site, or links the dimers and modifies the oxygen binding characteristics at the same time. Modifications such as chemical polymerization of globin chains, glycosylation, and pegylation, and/or encapsulation in a liposome or cell membranes are also contemplated.

In addition to extraction from animal sources, the genes encoding subunits of a desired naturally occurring or mutant hemoglobin (as herein defined) may be cloned, placed in a suitable expression vector and inserted into an organism, such as a microorganism, animal or plant, or into cultured animal or plant cells or tissues. These organisms may be produced using standard recombinant DNA techniques. Human alpha and beta globin genes have been cloned and sequenced by Liebhaber et al., *Proc. Natl. Acad. Sci. U.S.A.* 77; 7053–7058 (1980) and Marotta et al., *Journal of Biological Chemistry*, 252; 5040–5053 (1977) respectively. Techniques for expression of both wild-type and mutant alpha and beta globins and their assembly into a hemoglobin are set forth in Hoffman, S. J. and Nagai, K., U.S. Pat. No. 5,028,588 and Hoffman, S. J. et al., PCT/US90/02654, Townes, T. M. and McCune, S. L., PCT/US91/09624, Logan, J. S. et al., PCT/US92/05000, and Rausch, C. W. and Feola, M., European Patent Application 87116556.9. Individual globin chains have been reassorted with modified forms of globin chains to synthesize a semi-synthetic hemoglobin as well (Luisi et al., *Nature* 320; 555–556 (1986) and Nagai et al., *Nature* 329; 858–860 (1987)).

The hemoglobin produced by expression of recombinant DNA is most preferred as it lends itself to easy modification, is free of infectious agents and can be produced in unlimited supply. By applying the standard techniques of site specific mutagenesis to the globin gene(s), (Kruse et al., Biotechniques 6; 338–339 (1988) and Zoller et al., *Methods in Enzymology* 100; 468–500 (1987) are recent examples of site specific mutagenesis techniques) one can add, subtract or change any amino add or combination of amino acids in the resulting globin chain. Any of the hemoglobins or fragments thereof may be modified to alter the biological activity. For example, the modified hemoglobins or hemoglobin fragments may have altered oxygen affinity or serve as more potent hematopoietic growth factors (Hoffman and Nagai, U.S. Pat. No. 5,028,588; Hoffman et al., U.S. application Ser. No. 07/789,179).

For the purpose of the appended claims, a "hemoglobin" means a hemoglobin or hemoglobin-like protein comprised of one or more tetramers. Each tetraruer is composed of (a) two alpha globin-like and two beta globin-like polypeptides, (b) one di-alpha globin-like and two beta globin-like polypeptides, (c) two alpha globin-like and one di-beta globin-like polypeptides, (d) one di-alpha globin-like and one di-beta globin-like polypeptides, (e) one fused alpha/beta globin-like polypeptide and separate alpha and beta globin-like polypeptides, (f) two fused alpha/beta globin-like polypeptides (g) higher multiples of alpha globin-like and/or beta globin-like globins, e.g. four alpha globin-like subunits. The prefix "di-" before alpha or beta globin means that the C terminus of one alpha (or beta) subunit is linked to the N terminus of a second alpha (or beta) subunit either directly or through a peptide linker of one or more amino acids; the term "peptide bonds" is intended to embrace both possibilities. The di-alpha globin-like polypeptide preferably is capable of folding together with beta globin and incorporating heme to form functional hemoglobin-like protein. The di-beta globin-like polypeptide is analogously defined.

A globin subunit of one hemoglobin tetramer may be crosslinked or genetically fused to a globin subunit of another tetramer. A hemoglobin is said to be multimeric if it comprises more than four globin subunits or domains. The term "multimeric" thereby includes octameric hemoglobin (2 linked tetramers), as well as higher multimers as taught in co-pending PCT application Anderson et al., PCT publication number PCT/US92/09752 entitled Production and Use of Multimeric Hemoglobins.

A "genetically fused hemoglobin" is a hemoglobin-like protein comprising at least one "genetically fused globin-like polypeptide", the latter comprising two or more globin-like domains which may be the same or different.

It is also possible to provide an "alpha/beta globin-like pseudodimer" in which an alpha globin-like sequence is connected by peptide bonds to a beta globin-like sequence. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di-beta, or a alpha/beta globin-like polypeptide is a "pseudotetramer".

A human alpha globin-like domain or polypeptide is native human alpha globin or a mutant thereof differing from the native sequence by one or more substitutions, deletions or insertions, while remaining substantially homologous (as hereafter defined) with human alpha globin, and still capable of forming a tetrameric unit. A beta globin-like domain or polypeptide is analogously defined. Subunits of animal hemoglobins or mutants thereof and minor components of human hemoglobin or mutants thereof which are sufficiently homologous with human alpha or beta globin are embraced by the term "human alpha or beta globin-like domain or polypeptide." The alpha and beta globin-like polypeptides may be referred to collectively as "globins". For the sake of convenience the term "polypeptide" may refer to a unitary chain or to a domain of a longer polypeptide chain. Preferably, the globin-like domain or polypeptide has the ability to incorporate heme.

In determining whether a polypeptide is substantially homologous to alpha (or beta) globin, sequence similarity is an important but not exclusive criterion. Sequence similarity may be determined by conventional algorithms, which typically allow introduction of a small number of gaps in order to achieve the best fit. Preferably, the alpha globin-like polypeptides (or domains thereof) have at least about 75% sequence identity with wild-type human alpha globin. However, a polypeptide of lesser sequence identity may still be considered "substantially homologous" with alpha globin if it has a greater sequence identity than would be expected from chance and also has the characteristic higher structure of alpha globin and similar biological activity. By way of comparison, Artemia's heme-binding domains are considered homologous with myoglobin even though the primary sequence similarity is no more than 27%. Alignment of the heme-binding domains around conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues. Moreover, among the serine protease inhibitors there are families of proteins recognized to be homologous in which there are pairs of members with as little as 30% sequence homology.

Well over a hundred mutants of human hemoglobin are known, affecting both the alpha and beta chains, and the effect of many of these mutations on oxygen-binding and other characteristics of hemoglobin is known. The human alpha and beta globins themselves differ at 84 positions. Interspecies variations in globin sequence have been extensively studied. Dickerson, *Hemoglobin Structure, Function, Evolution and Pathology* ch. 3 (1983) reported that in 1982, the 60 known vertebrate alpha globins had identical residues at 23 of their 141 positions, while for the 66 vertebrate beta globins considered, 20 of the 146 amino acids are identical. The 60 vertebrate myoglobins, which also belong to the globin family, had 27 invariant amino acids out of 153 positions. If only mammals are considered, then ~35% of the both the alpha and beta globin amino adds are invariant. Invariant positions cluster around the centers of activity of the molecule: the heme crevice and the intersubunit contacts. Of the variable amino adds, some diverge from the consensus sequence for only a small fraction of the species considered. The number of total differences between human alpha globin and other homologous vertebrate alpha globins is as follows: rhesus monkey (4), cow (17), platypus (39), chicken (35), human zeta (embryonic) (61), carp (71), and shark (88). For invertebrate globins the divergences within the homologous family include: sea lamprey (113), mollusc (124), Glycera (marine bloodworm) (124) and Chironomus (midge) (131). The differences between human beta globin and other homologous vertebrate beta globins include: rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), Glycera (125) and Chironomus (128).

Many of these differences may be misleading—variable amino acids may exhibit only "conservative substitutions" of one amino acid for another, functionally equivalent one. A "conservative substitution" is a substitution which does not abolish the ability of a globin-like polypeptide (or domain) to incorporate heme and to associate with alpha and beta globin subits to form a tetrameric (or pseudotetrameric) hemoglobin-like protein. The following resources may be used to identify conservative substitutions (and deletions or insertions):

(a) data on hemoglobin mutants (over a hundred such mutants exist);

(b) data on sequence variations among vertebrate, especially mammalian, alpha globins and beta globins;

(c) data on sequence variations among vertebrate, especially mammalian, myoglobins;

(d) data on sequence variations between vertebrate and invertebrate globins or among the invertebrate globins;

(e) data on the three-dimensional structures of human hemoglobin and other substantially homologous proteins coupled with molecular modeling software for predicting the effect of sequence changes on such structures; and (f) data on the frequencies of amino acid changes between members of families of homologous proteins (not limited to the globin family). See, e.g., Table 1–2 of Schulz and Schirmer, *Principles of Protein Structure* (Springer-Verlag: 1979) and FIGS. 3–9 of Creighton, *Proteins Structure and Molecular Properties* (W. H. Freeman: 1983).

While the data from (a)–(d) are most useful in determining tolerable mutations at the site of variation in the cognate proteins, it may also be helpful in identifying tolerable mutations at analogous sites elsewhere in the molecule. Based on the data in category (f), the following exchange groups may be identified, within which substitutions of amino acids are frequently conservative:

I. small aliphatic, nonpolar or slightly polar residue—Ala, Ser, Thr (Pro, Gly)

II. negatively charged residue and their amides—Asn Asp Glu Gln

III. positively charged residues—His Arg Lys

IV. large aliphatic nonpolar residues—Met Leu Ile Val (Cys)

V. large aromatic residues—Phe Tyr Trp

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding. Note that Schulz and Schimer would merge I and II above. Note also that Tyr, because of its hydrogen bonding potential, has some kinship with Ser, Thr, etc. Therefore, any of the aforementioned hemoglobins obtained from any of the aforementioned sources are contemplated as suitable for the present invention once the hemoglobin is in purified form.

Purification of extracellular hemoglobin can be accomplished using techniques which are well known in the art. For example, hemoglobin can be isolated and purified from outdated human red blood cells by hemolysis of erythrocytes followed by cation exchange chromatography (Bonhard, K., et al., U.S. Pat. No. 4,439,357), anion exchange chromatography (Tayot, J. L. et al., EP Publication 0 132 178), affinity chromatography (Hsia, J. C., EP Patent 0 231 236 B1), filtering through microporous membranes (Rabiner, S. F. (1967) et al., J. Exp. Med. 126: 1127–1142), heating a deoxygenated solution of semi-purified hemoglobin to precipitate contaminants (Estep, T. N., PCT publication PCT/US89/014890, Estep, T. N., U.S. Pat. No. 4,861,867), precipitating contaminants by the addition of polyvalent ions and polysulfates (Simmonds, R. S. and Owen, W. P., U.S. Pat. No. 4,401,652) or precipitating the hemoglobin itself with zinc followed by resuspension (Tye, R. W., U.S. Pat. No. 4,473,494). Hemoglobin can also be purified from other sources, e.g. bovine blood, and treated by any of the methods above or by microporous filtration, ultrafiltration and finally ion exchange chromatography (Rausch, C. W. and Feola, M., EP 0 277 289 B1) or by ultrafiltration alone (Kothe, N. and Eichentopf, B. U.S. Pat. No. 4,562,715). Recombinant hemoglobins produced in transgenic animals have been purified by chromatofocusing (Townes, T. M. and McCune, PCT publication PCT/US/09624); those produced in yeast have been purified by ion exchange chromatography (Hoffman, S. J. and Nagai, K. in U.S. Pat. No. 5,028,588 and Hoffman, et al., WO 90/13645). Particularly preferred methods of purifying recombinant hemoglobin are described in co-pending patent applications Ser. No. 08/097,273, filed Jul. 23, 1993, entitled Nickel Free Hemoglobin and Methods for Producing Such Hemoglobins; Ser. No. 07/789,179, filed Nov. 8, 1991, entitled Production in Bacteria and Yeast of Hemoglobin and Analogues Thereof and Ser. No. 08/153,071, filed Nov. 15, 1993, entitled Method for the Rapid Removal of Protoporphyrin IX from Protoporphyrin IX-Containing Solutions of Hemoglobin.

Although dearly hemoglobin has been purified from a number of different sources by a number of different techniques, it is only recently that pure hemoglobin solutions have become available that are also stabilized against dimer formation. Prior to the introduction of highly uniform micro and ultrafiltration membranes and high selectivity chromatography columns and crosslinking chemistries in the late 1960's, all so-called purified or stroma-free hemoglobin was in fact contaminated with cellular components and was subject to the formation of dimers (Winslow, W. M. (1992) *Hemoglobin-based Red Cell Substitutes*, The Johns Hopkins University Press, Baltimore, 242 pp). These contaminants in the hemoglobin and/or the dimerization of uncrosslinked or otherwise stabilized hemoglobin led to nausea, vomiting, myalgia, nephrotoxidty, complement activation, febrile responses, and bradychardia (Winslow, W. M. (1992) *Hemoglobin-based Red Cell Substitutes*, The Johns Hopkins University Press, Baltimore, 242 pp). Even those chemically crosslinked hemoglobins that have been properly purified may still harbor viruses, retain small amounts of uncrosslinked hemoglobins, or contain small quantities of potentially toxic unreacted crosslinker. As a result, a preferred hemoglobin is recombinantly derived hemoglobin, more preferably hemoglobin produced in *E. coli* containing at least a mutation to stabilize against the formation of dimers, most preferably hemoglobin produced in *E. coli* containing at least a mutation to stabilize against the formation of dimers and a mutation to alter oxygen affinity (designated rHb1.1) described in copending patent application Ser. No. filed Nov. 8, 1991, entitled Production in Bacteria and Yeast of Hemoglobin and Analogues Thereof, and produced and purified using the methods described in copending patent application Ser. No. 08/097,273, filed Jul. 23, 1993, entitled Nickel Free Hemoglobin and Methods for Producing Such Hemoglobins or co-pending patent application Ser. No. 07/789,179, filed Nov. 8, 1991, entitled Production in Bacteria and Yeast of Hemoglobin and Analogues Thereof.

Purified hemoglobin in any of the aforementioned forms, from any of the aforementioned sources and purified by any of the aforementioned methods, can be useful, either alone or in combination with other components to:

(1) stimulate hematopoiesis;

(2) treat mammals suffering from a cytopenia, such as anemia or thrombocytopenia;

(3) treat mammals suffering from a cachexia associated with a cytopenia, such as cachexia associated with AIDS or AZT therapy for AIDS;

(4) act as an active ingredient in a pharmaceutical composition to treat mammals suffering a cytopenia, particularly anemia or thrombocytopenia;

(5) in combination with other hematopoietic factors, either alone or as part of a pharmaceutical composition, to treat mammals suffering from a cytopenia, particularly anemia or thrombocytopenia;

(6) act as an active ingredient in a pharmaceutical composition to treat mammals suffering from a cachexia associated with a cytopenia, such as cachexia associated with AIDS or AZT therapy for AIDS;

(7) in combination with other hematopoietic factors, either alone or as part of a pharmaceutical composition, to treat mammals suffering from a cachexia associated with a cytopenia, such as cachexia associated with AIDS or AZT therapy for AIDS;

(8) as a component, either alone or in combination with other hematopoietic factors, as an additive to cell culture media to enhance or stimulate ex vivo expansion of blood cells and progenitors.

The present invention provides for such pharmaceutical compositions and formulations for stimulation of hematopoiesis, treatment of anemia, treatment of cytopenias, ex vivo expansion of blood cells, and cell culture additive. The compositions of the invention can be incorporated in conventional solid or liquid pharmaceutical formulations (e.g. tablets, capsules, caplets, injectable or orally administratable solutions) for use in treating mammals in need thereof. The pharmaceutical formulations of the invention comprise a physiologically and/or pharmaceutically and/or therapeutically effective amount of the hemoglobin of the present invention as the active ingredient alone or in combination with other active or inert agents. For example, a parenteral therapeutic composition may comprise a sterile isotonic saline solution containing between 0.1 percent and 90 percent weight to volume of hemoglobin. A preferred hemoglobin solution contains from 1 percent to 10 percent hemoglobin, most preferably about 5 percent hemoglobin weight to volume. In addition, the physiologically acceptable solution also includes 0–200 mM of one or more physiological buffers, 0–200 mM of one or more carbohydrates, 0–200 mM of one or more alcohols or poly alcohols, 0–200 mM of one or more physiologically acceptable salts, and 0–1% of one or more surfactants, and is at pH 6.9–7.9. More preferably, the physiologically acceptable solution contains 0–50 mM Na bicarbonate, 0–50 mM of one or more carbohydrates (e.g. glucose, mannitol, sorbitol or others known to the art), 0–150 mM of one or more chloride salts and 0–0.5% surfactant, e.g. Tween™ [polysorbate 80]. Even more preferably, the physiologically acceptable solution contains 0–25 mM Na bicarbonate, 0–50 mM mannitol or lactose, 0–100 mM NaCl, 0–25 mM $CaCl_2$, 0–25 mM $MgCl_2$, 0–25 mM KCl and 0–0.5% surfactant, e.g. Tween™ [polysorbate 80], pH 7.0–7.8. Most preferably, the physiologically acceptable pharmaceutical composition includes 5 mM Na bicarbonate, 100 mM NaCl, 50 mM mannitol, 2 mM $CaCl_2$, 1 mM $MgCl_2$, 3 mM KCl and 0.03% Tween™ 80,pH 7.5–7.7. Other components may be added if required, such as reducing agents, anti-oxidants, anti-bacterial agents, oncotic pressure agents (e.g. albumin or polyethylene glycols) and other physiologically acceptable salts and sugars. An alternative suitable formulation for purified recombinant hemoglobin is 150 mM NaCl, 5 mM sodium phosphate, pH 7.4.

The therapeutically effective quantity of pharmaceutical provided to the individual is sufficient to provide a blood concentration of between 0.0001 micromolar and 1 millimolar of hemoglobin. In contrast to Feola et al., (1992) Surg. Gyn. Obstet. 174: 379–386, who injected over 1.7 gm of hemoglobin per kilogram body weight, the method of the present invention results in hematopoiesis at a low dose of hemoglobin, typically from 1 ng to 1 gram of hemoglobin per kilogram of patient body weight. Dosages can be from 0.001–1000 mg hemoglobin/kg body weight, more preferably 0.01 mg–100 mg hemoglobin/kg body weight, most preferably 1 mg to 10 mg hemoglobin/kg body weight.

It will be appreciated that the unit content of active ingredients contained in an individual dose of each dosage form need not in itself constitute an effective amount since the necessary effective amount can be reached by administration of a plurality of capsules, tablets, injections, etc. or combinations thereof.

Each formulation according to the present invention may additionally comprise inert constituents including pharmaceutically-acceptable carriers, diluents, fillers, salts, and other materials well-known in the art, the selection of which depends upon the dosage form utilized, the condition being treated, the particular purpose to be achieved according to the determination of the ordinarily skilled artisan in the field and the properties of such additives.

The pharmaceutical compositions of the invention may be administered to an individual by any conventional means such as orally, by aerosol, by transdermal adsorption, by adsorption through a mucus membrane or by injection. Parenteral administration is preferred, particularly intravenously or intraarterial.

Administration of hemoglobin can occur for a period of minutes to weeks; however the usual time course is over the course of several weeks to gain maximum hematopoietic effect and ameliorate the course of a cytopenia. Typical administration regimes can be from one to ten weeks, more preferably four to nine weeks, most preferably six to eight weeks.

Dosages of hemoglobin can be administered at a frequency of 1 to 7 times per week, more preferably 2 to 5 times per week, most preferably 3 times per week.

The method of the present invention is useful for the treatment of cytopenia in a mammal. Cytopenias are conditions wherein any of the circulating blood cells are reduced. Each of the cytopenias is characterized by various reductions in levels of circulating blood cells and can be broadly defined. For example, the term "anemia" refers to a condition in which the blood is deficient in red blood cells, in hemoglobin or in total volume. Anemia is usually determined by comparing either hemoglobin (grams/deciliter), hematocrit (percentage of blood volume occupied by red blood cells) or red blood cell count (number of red blood cells×$10^6$/microliter) with "normal" values. These normal values are arbitrarily set as the mean±2 standard deviations of values in a healthy population (Table 1).

TABLE 1

| Normal Ranges of Blood Parameters in Adults(*) | |
|---|---|
| Hemoglobin (gm/dl) | 12.0–17.7 |
| Hematocrit (%) | 36–52 |
| Red Blood Cells (×106/ul) | 4.0–6.0 |
| Mean Cell Volume (fl) | 80–100 |

(*)Adapted from Nathan, D.G. in Cecil Textbook of Medicine, (1992), J. B. Wyngaarden, L. H. Smith and J. C. Bennett, ed. W. B. Saunders Co, Philadelphia, pages 817–836

However, these normal ranges must be adjusted for persons living at altitude as well as for differences in race and gender. Anemia may be masked by dehydration, where reduced plasma volume yields apparently normal hemoglobin concentrations, and likewise anemia can be mimicked by increased plasma volume, as in pregnancy. Thus the diagnosis of anemia can be made using published values as a guideline, but must be determined by a clinician skilled in the art. The other cytopenias, such as neutropenia and thrombocytopenia are likewise difficult to define. For example, neutropenia is generally considered to occur when the circulating neutrophil count falls below 2.0×$10^9$ per liter, however, this normal range is reduced in several population groups. Thrombocytopenia is defined as platelet counts<100,000 per microliter. Again, this number is a guideline for the diagnosis of thrombocytopenia, but the final diagnosis must be made by a clinician skilled in the art.

The cytopenias can occur as the result of a suite of underlying conditions. For example, many AIDS patients develop anemia as the restfit of the course of the disease itself, or of the therapeutic interventions required to manage the disease. Chronic AZT administration to AIDS patients acts as an anti-metabolite and disrupts normal hematopoiesis. The present invention is particularly useful in reversing the cytopenias induced by AZT therapy, and moreover ameliorating the accompanying cachexia caused by either the AZT therapy or the AIDS disease.

In chronic renal failure there is inadequate production of erythropoietin resulting in only marginal erythropoiesis and symptomatic chronic anemia. Regular administration of recombinant hematopoietic growth factor erythropoietin to dialysis patients with anemia due to chronic renal failure results in sustained erythropoiesis and an increased hematocrit. However, continued erythropoietin therapy in this disease state frequently results in iron deficiency that can limit the long term effectiveness of this treatment modality. Administration of oral or intravenous iron therapy can replenish these iron stores, but some anemic chronic renal failure patients on dialysis either cannot absorb oral iron or will not take it due to side effects. The administration of intravenous iron dextran may be attempted in these particularly refractive cases, but such administration may lead to anaphylactic shock.

Other diseases that may lead to cytopenias include but are not limited to liver disease, endocrine disorders such as hypothyroidism, myelodysplastic syndrome, sideroblastic anemias, sickle cell anemias, thalassemias, certain drug, environmental or industrial toxicities, autoimmune disorders such as rheumatoid arthritis, cancers, chemotherapy and radiotherapy and the like. Any of these cytopenias will be alleviated by low dose administration of the hemoglobin of the present invention.

Additionally, the present invention is useful to enhance ex vivo expansion of blood components when a purified hemoglobin solution is added to a culture medium. The addition of hemoglobin to a cell culture may be as part of the pharmaceutical compositions described above or as part of a different buffered solution. Ex vivo expansion of blood components, particularly those in the erythroid cell line, can be accomplished by first harvesting progenitor cells from bone marrow, the circulation, the spleen or fetal liver, growing up the cells in appropriate media and inducing differentiation and growth with suitable growth factors (Tsukamoto, A., et at. U.S. Pat. No. 5,061,620; Palsson, B. O., et at., PCT publication PCT/US93/01803; Emerson, S. G. et al., PCT publication PCT/US91/09173; Boyse, E. A., et al., PCT publication PCT/US88/04044; Shih, C.-C., PCT publication PCT/US93/01852; Sardonini, C. et al., PCT publication PCT/US93/02043). After collection and expansion, the hematopoietic cells can be re-infused into a patient, for example, after a bone marrow transplant, or the hematopoiefic cells can be genetically adjusted to repair a genetic error, such as thalassemia or sickle cell anemia and subsequently re-infused into a patient. Because growth factors work in a synergistic fashion, the addition of hemoglobin to the suite of possible growth factors will allow greater cell growth and differentiation of more lines that had been previously possible.

The present invention is also useful for potentiating chemotherapeutic or radiotherapeutic treatment modalities. Growth factors have been used to induce leukemic progenitor cells into cycle and render them more susceptible to chemotherapeutic agents or radiotherapy (Mertelsmann, R. H. (1993) in *Application of Basic Science to Hematopoiesis and the Treatment of Disease*, E. D. Thomas and S. K. Carter (ed)). The treatment of a cancer patient with hemoglobin either prior to, concurrently with or immediately subsequent to chemotherapeutic or radiotherapeutic intervention will increase the lethality of the cytotoxic agent, whether the cytotoxic agent is in the form of chemotherapy or radiotherapy.

Moreover, the present invention is useful for enhancement of growth of progenitor cells in culture, by addition of hemoglobin, either alone or in combination with other growth factors, to the culture medium. These progenitor cells grown by this method can then be used in diagnostics, in the production of further growth factors, and for the development of model systems useful for understanding in vivo hematopoiesis. The growth of progenitor cells is well known in the art and can be achieved as described in Tsukamoto, A., et al. U.S. Pat. No. 5,061,620; Palsson, B. O., et al., PCT publication PCT/US93/01803; Emerson, S. G. et al., PCT publication PCT/US91/09173; Boyse, E. A., et al., PCT publication PCT/US88/04044; Shih, C.-C., PCT publication PCT/US93/01852; Sardonini, C. et al., PCT publication PCT/US93/02043, Cipolleschi, M. G. et al., (1993) Blood 82: 2031–2037, Abraham, N. G. et al., (1991) Acta FIaematol. 86: 189–193; Chertkov, J. L. et al., (1992) J. Lab. Clin. Med. 119: 412–419.

The present invention also contemplates the use of additional hematopoietic factors, which when administered in combination with purified hemoglobin, stimulate hematopoiesis to a degree greater than either therapeutic compound alone. Examples of such additional hematopoietic factors include but are not limited to Granulocyte-Macrophage Colony Stimulating Factor (GM-CSF), Macrophage Colony-Stimulating Factor (M-CSF), Granulocyte Colony-Stimulating Factor (G-CSF), Stem Cell Factor (SCF), Erythropoietin (EPO) and Interleukins 1–13 (IL1 to IL13) [Souza, L. M., U.S. Pat. No. 4,810,643; Clark, S. C. and Wong, G. G., U.S. Pat. No. 4,868,119; Biasdale, J. H. C., European Patent EP 355093; Quesenberry, P. J. in *Hematology*, W. J. Williams, E. Beutler, A. J. Erslev and M. A. Lichtman (eds) 1990, McGraw-Hill, Inc. New York, pp 129–147; Lin, U.S. Pat. No. 4,703,008; Zsebo, K. M. et al., PCT/US90/05548; Nicola, N. A. (1993) in *Application of Basic Science to Hematopoiesis and the Treatment of Disease*, E. D. Thomas and S. K. Carter (ed), Raven Press, New York; Deeley M., et al., U.S. Pat. No. 5,023,676).

Administration of purified hemoglobin in combination with other additional hematopoietic factors can be together in the same dosage formulation or can be divided and administered individually to achieve maximum therapeutic effect. The optimal dosage regime can be determined by dinidans of ordinary skill in the art.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references cited herein are hereby incorporated by reference for their relevant teachings.

EXAMPLES

The following examples are provided by way of describing specific embodiments of the present invention without intending to limit the scope of the invention in any way.

Example 1

Enhancement of Growth of Burst Forming Units—Erythroid (BFU-E) Collected from Normal (BDF1) Mice by Treatment with Purified Recombinant Hemoglobin Hemoglobin was prepared and formulated as described in co-pending patent application Ser. No. 08/097,273,filed Jul. 23, 1993,entitled Nickel Free Hemoglobin and Methods for Producing Such Hemoglobins. Bone marrow was collected from normal BDF1 mice (8–12 weeks old, Charles River, Wilmington, Del.). The bone marrow culture techniques used in these studies have been previously described (Abraham, N. et al., (1989) Blood 74: 139–144) and are well known in the art. Briefly, bone marrow erythroid colonies (burst forming unit-erythrocyte—BFU-E) were grown in 1.12% methylcellulose containing 0.4 U/ml erythropoietin for 5 days. Three concentrations of purified recombinant hemoglobin (1 uM, 10 nM and 0.1 nM) were added to different cultures treated with 0.01, 0.1, 1 and 10 uM of AZT. All cultures were run in triplicates and generally 9–12 determinations were made for each point. BFU-E growth was scored at 3 days.

Figure 1:
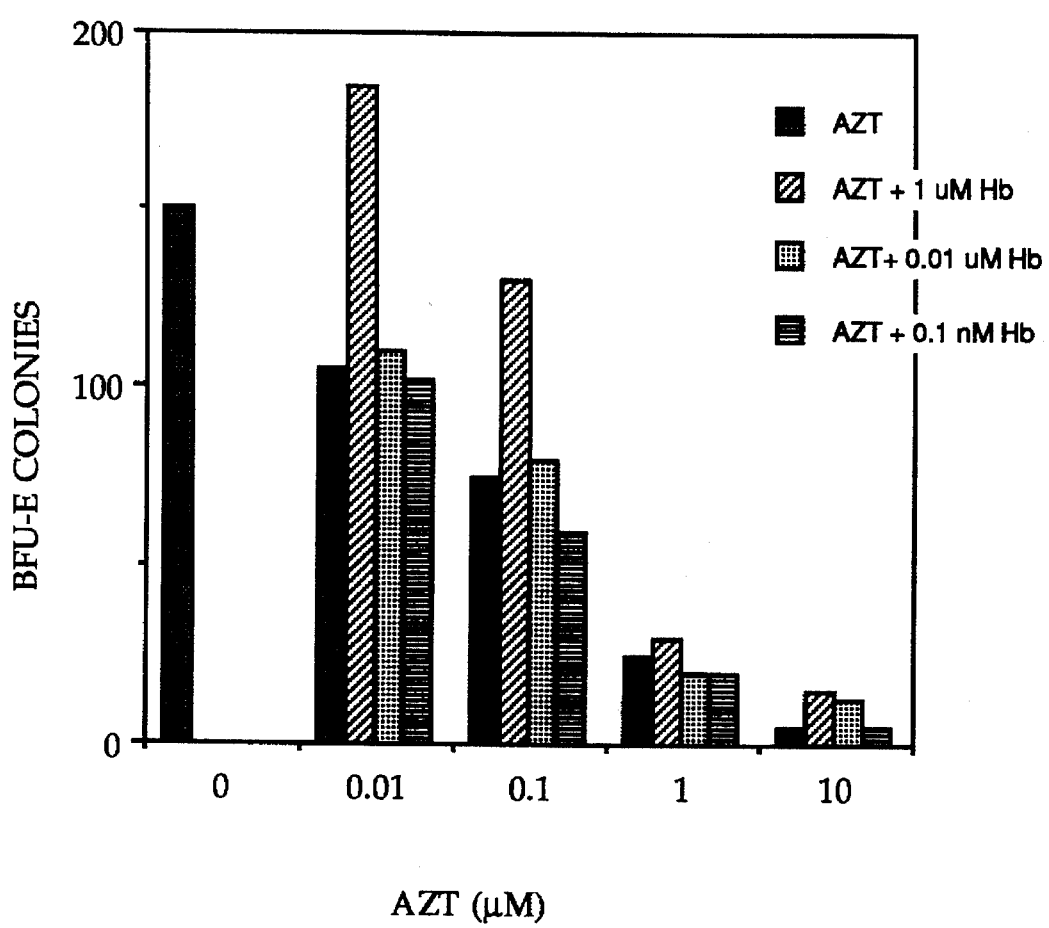
FIG. 1 is a representation of the number of BFU-E colonies counted in cell cultures 10 days after of addition of 1 uM, 0.01 uM or 0.1 nM of hemoglobin to cultures of normal BDF1 murine bone marrow that had been grown in the presence of 0.01, 0.1, 1 and 10 uM of AZT.

As seen in FIG. 1, AZT inhibits BFU-E colony formation in a dose dependent manner in normal BDF1 mice. Hemoglobin at a concentration of 1 uM was able to reverse these effects at concentrations of AZT of less than 1 uM (FIG. 1). Note that concentrations of hemoglobin equal to or greater than 10 and 100 uM resulted in increases of BFU-E beyond the level measurable in this assay and were thus not reported.

Example 2

Figure 2:
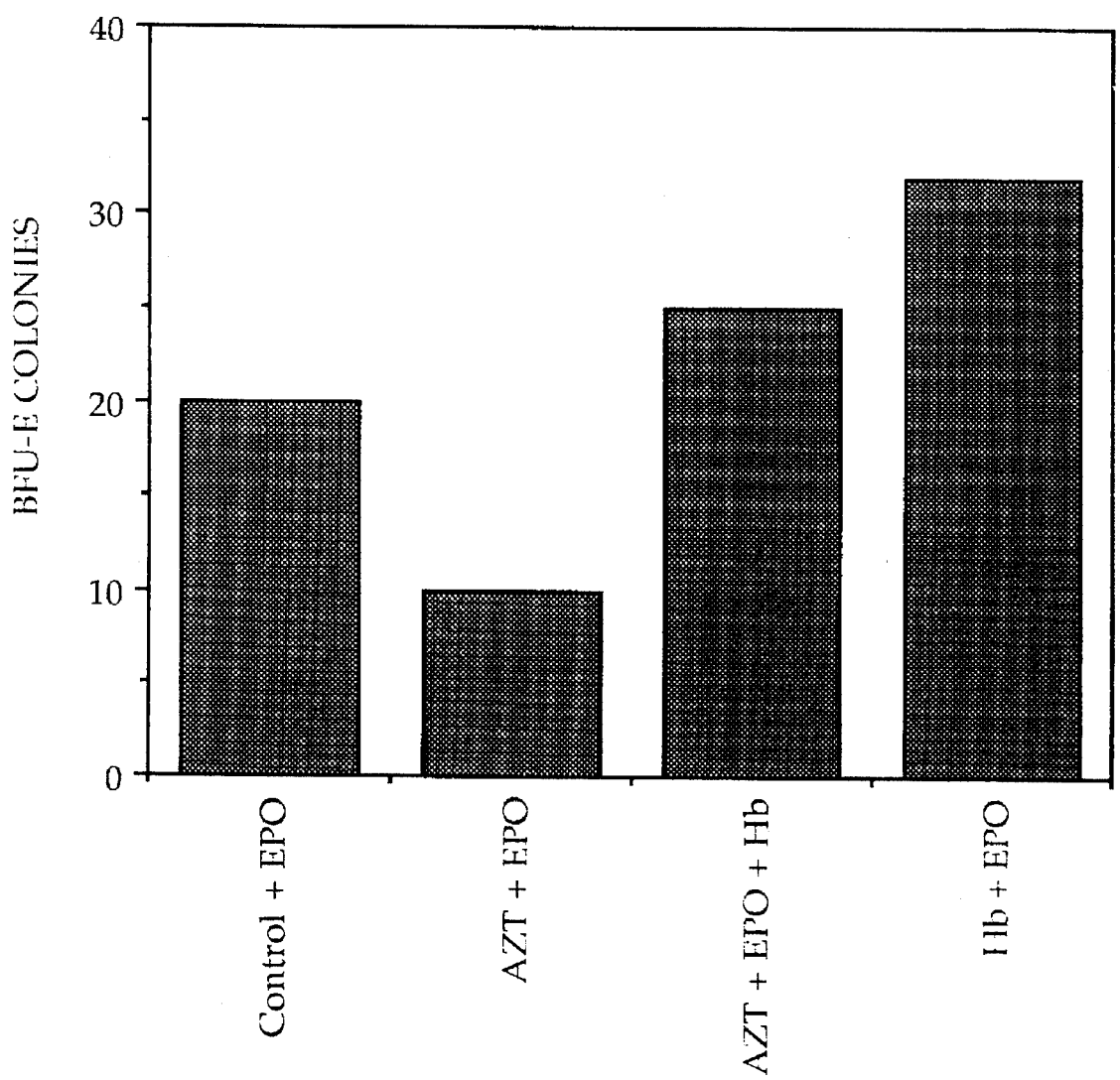
FIG. 2 is a representation of the number of BFU-E colonies counted in cell cultures both without hemoglobin and 10 days after of addition of 1 uM hemoglobin to cultures of SCID mouse bone marrow cells that had been grown in the presence of 0.4 U/mL of EPO and/or 0.01 uM AZT.

Enhancement of BFU-E Growth with Purified Recombinant Hemoglobin—SCID Mouse Bone Marrow Bone marrow mononuclear BFU-E's were collected from SCD mice (Severely Combined Immunodeficient Disorder mice, 8—12 weeks old, Taconic Farms, Germantown, N.Y.), and grown as described above in Example 1. rHb1.1 at a concentration of 1 uM was able to reverse the effect of 0.1 uM AZT (FIG. 2).

Example 3

Figure 3:
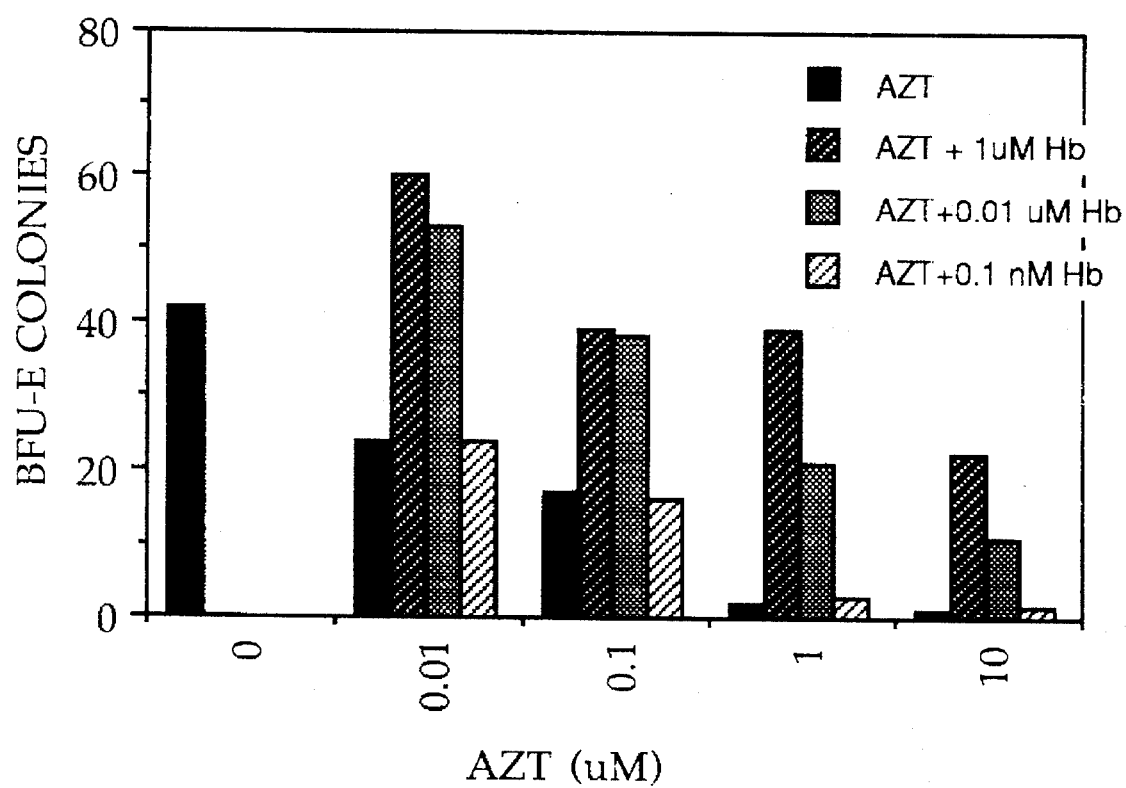
FIG. 3 is a representation of the number of BFU-E colonies counted in cell cultures 10 days after of addition of 1 uM, 0.01 uM or 0.1 nM of hemoglobin to cultures of human bone marrow that had been grown in the presence of 0.01, 0.1, 1 and 10 uM of AZT.

Enhancement of BFU-E Growth with Purified Recombinant Hemoglobin—Human Bone Marrow Culture The experiment described in Example 1 was performed exactly as described in the example 1, except for the utilization of normal human bone marrow collected from normal volunteers. As in the experiment described in Example 1, 1 uM of recombinant purified hemoglobin added to the culture system was able to reverse AZT toxicity at concentrations of AZT less than 1 uM. The results of this in vitro experiment are shown in FIG. 3.

Example 4

Enhancement of BFU-E Erythropoiesis in vivo—Normal (BDF-1) Mouse

BFU-E cells in the bone marrow are early precursors of red blood cells. The effect of rHb1.1 on BFU-E cells was evaluated by measuring BFU-E in the bone marrow of mice after suitable treatment. Normal BDF1 mice were made anemic by administration of AZT (2.5 mg/ml) in their drinking water for 5 weeks. Normal controls, (normal BDF1 mice 8–12 weeks old, Charles River, Wilmington, Del.) were held for the same period of time, with no AZT added to the drinking water. Treatment with either recombinant human erythropoietin (EPO, Toyoba, Osaka Japan) or recombinant hemoglobin or a combination of these two treatments was initiated after 5 weeks of AZT exposure. Mice were continued on AZT during the three week dosing schedule of therapeutics. Body weight and blood indices were determined by routine methods. Groups of mice consisting of 4 to 12 mice per group were used. These groups were:

(1) normal controls,
(2) AZT-treated animals
(3) AZT/EPO (10 U/mouse)
(4) AZT/EPO/0.5 mg recombinant purified hemoglobin/kg of body weight
(5) AZT/EPO/1.0 mg recombinant purified hemoglobin/kg of body weight
(6) AZT/0.5 mg recombinant purified hemoglobin/kg of body weight
(7) AZT/1.0 mg recombinant purified hemoglobin/kg of body weight If the mouse received erythropoietin, ten units of recombinant human erythropoietin (Toyobo, Osaka, Japan) [equivalent to ~500 U/kg, a normal dose of erythropoietin used for the treatment of AZT-induced anemia in humans] was administered subcutaneously 3 times per week. Mice also received hemoglobin intravenously at a dose of either 0.5 or 1.0 mg/kg three times per week. Recombinant hemoglobin solution was prepared in phosphate buffered saline, pH 7.4.

Figure 4:
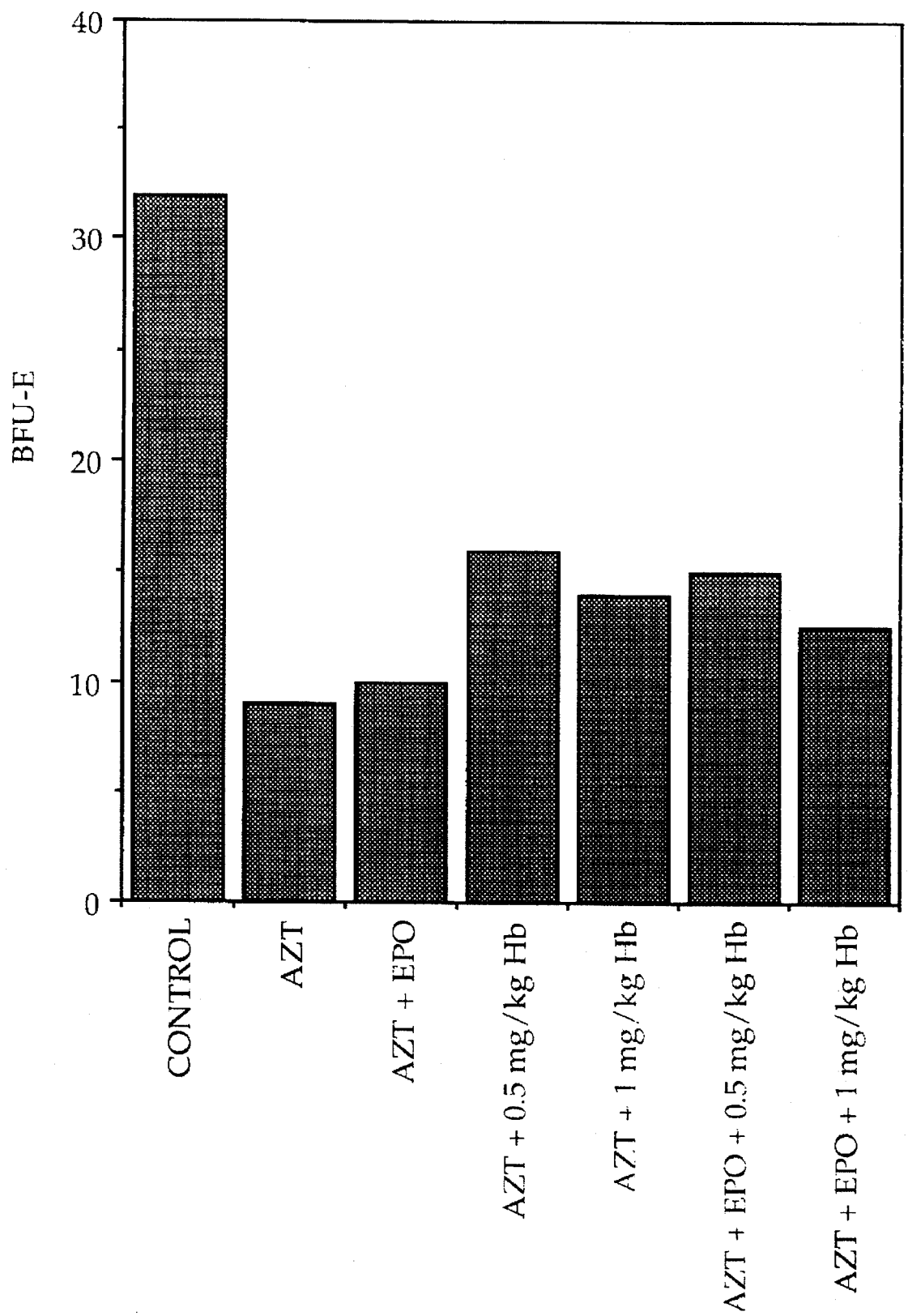
FIG. 4 is a graphical representation of Burst Forming Units—Erythroid (BFU-E) in BDF1 mice following three weeks of administration of either.

After the five week period, the AZT-treated mice showed marked anemia, thrombocytopenia and leukopenia. Hemoglobin administration resulted in increased BFU-E's (FIG. 4). As seen in FIG. 4, recombinant hemoglobin significantly increased the number of BFU-E in AZT treated normal BDF1 mice. Stimulation of this cell type was not seen with EPO in these models, a finding which is consistent with previous studies showing a minimal effect of EPO on the earlier red cell progenitors following AZT treatment (Abraham, N. (1989) Blood 74: 139–144).

Example 5

Increase of Hematocrit in vivo with Treatment with Purified Recombinant Hemoglobin—Normal (BDF-1) Mouse Hematocrit, the ratio of the volume of packed red blood cells to the volume of whole blood, was measured in the mice treated as described in Example 4. Hemoglobin produced a more substantial reversal of hematocrit suppression than EPO alone administered at 10U/mouse and appeared to act independently of exogenously administered EPO when the two agents were added together. As seen if FIG. 5, this enhancement of erythropoiesis was manifested as an increased hematocrit.

In a mouse with AZT induced anemia, the hematocrit falls to approximately 20%; if we assume that there are 5 mmol Hb/L of RBC or 0.005 mmol Hb/ml of RBC, and a mouse has a total blood volume of 3 ml, then approximately 20% (0.6 mls) of that blood volume is red blood cells. This 0.6 mls of RBC contains 0.003 mmols of Hb or 0.012 mmols of Fe. If we administer a total of 9 ug of Hb/gm of body weight and assume that a mouse weighs 200 gm, then the mouse has received a total of 0.028 umoles of Hb or 0.1125 umoles of Fe. However, this administration of Hb has resulted in an unexpected rise in hematocrit to ~40% (in the worst case, AZT+Hb, 1.0). The hematocrit approximately doubled from 20 to 40% (again assuming 3 mls of total blood volume, from 0.6 mls to 1.2 mls), requiring the synthesis of 3 umols of Hb which in turn required 120 umoles of Fe. Therefore the hemoglobin acted not simply as an iron source but actually as an erythropoietic factor.

Example 6

Increase of Cell Count in vivo with Treatment with Purified Recombinant Hemoglobin—Normal (BDF-1) Mice Both white blood cell and red blood cell counts were measured in the mice treated as described in Example 4. Hemoglobin produced a more substantial reversal of blood count suppression than EPO alone administered at 10U/mouse and appeared to act independently of exogenously administered EPO when the two agents were added together. As seen if FIG. 6, this enhancement of hematopoiesis was manifested as an increased counts of both cell types, indicating a broad hematopoietic effect of low dosage hemoglobin administration.

Example 7

Enhancement of BFU-E Erythropoiesis in vivo—SCID Mice

BFU-E cells in the bone marrow are early precursors of red blood cells. The effect of rHb1.1 on BFU-E cells was evaluated by measuring BFU-E in the bone marrow of mice after suitable treatment. SCID mice were made anemic by administration of AZT (2.5 mg/ml) in their drinking water for 5 weeks. SCID mice have been used previously as models for the immunodefidency seen in humans infected with HIV-1, the infectious agent in AIDS (Aldrovandi, G. M. et al., (1993) Nature 363: 732–6). Normal controls, (normal BDF1 mice 8–12 weeks old, Charles River, Wilmington, Del.) were held for the same period of time, with no AZT added to the drinking water. Treatment with either recombinant human erythropoietin (EPO, Toyoba, Osaka Japan) or recombinant hemoglobin or a combination of these two treatments was initiated after 5 weeks of AZT exposure. Mice were continued on AZT during the three week dosing schedule of therapeutics. Body weight and blood indices were determined by routine methods. Groups of mice consisting 4 to 12 mice per group were used. These groups were:

(1) normal controls,
(2) AZT-treated animals
(3) AZT/EPO (10 U/mouse)
(4) AZT/EPO/0.5 mg recombinant purified hemoglobin/kg of body weight
(5) AZT/EPO/1.0 mg recombinant purified hemoglobin/kg of body weight
(6) AZT/0.5 mg recombinant purified hemoglobin/kg of body weight
(7) AZT/1.0 mg recombinant purified hemoglobin/kg of body weight If the mouse received erythropoietin, ten units of recombinant human erythropoietin (Toyobo, Osaka, Japan) [equivalent to ~500 U/kg, a normal dose of erythropoietin used for the treatment of AZT-induced anemia in humans] was administered subcutaneously 3 times per week. Mice also received hemoglobin intravenously at a dose of either 0.5 or 1.0 mg/kg three times per week. Recombinant hemoglobin solution was prepared in phosphate buffered saline, pH 7.4.

After the five week period, the AZT-treated mice showed marked anemia, thrombocytopenia and leukopenia. Hemoglobin administered in dosages of 0.5 or 1 mg/kg body weight resulted in increased BFU-E's (FIG. 7) in the SCID mice.

Example 8

Increase of Cell Count in vivo with Treatment with Purified Recombinant Hemoglobin—SCID Mice Both white blood cell and red blood cell counts were measured in the mice treated as described in Example 7. Hemoglobin produced a more substantial reversal of blood count suppression than EPO alone administered at 10U/mouse and appeared to act independently of exogenously administered EPO when the two agents were added together. As seen if FIG. 8, this enhancement of hematopoiesis was manifested as an increased counts of both cell types, indicating a broad hematopoietic effect of low dosage hemoglobin administration.

Example 9

Influence of Hemoglobin on AZT-induced Body Weight Loss—Normal Mice

In addition to hematopoietic suppression, another manifestation of AZT toxicity is weight loss (cachexia), an observation that is often manifested in AIDS patients. Cachexia is considered a reliable prognostic indicator for clinical outcome in AIDS (Huang et al., (1998) Clin. Chem., 34: 1957–1959). Body weight was measured for the mice treated as described in Example 4. As seen in FIG. 9, AZT induced a significant suppression in body weight in BDF-1 mice whereas hemoglobin alone was able to alleviate this manifestation of AZT toxicity.

Example 10

Influence of Hemoglobin on AZT-induced Body Weight Loss—SCID Mice

In addition to hematopoietic suppression, another manifestation of AZT toxicity is weight loss (cachexia), a observation that is often manifested in AIDS patients. Cachexia is considered a reliable prognostic indicator for clinical outcome in AIDS (Huang et al., (1998) Clin. Chem., 34: 1957–1959). Body weight was measured for the mice treated as described in Example 7. As seen in FIG. 10, AZT induced a significant suppression in body weight in SCID mice whereas hemoglobin alone was able to alleviate this manifestation of AZT toxicity.

Example 11

Spleen Colony-Forming Unit (CFU-S) Determination

To evaluate whether hemoglobin was acting at a level other than the committed erythroid precursor (CFU-E, BFU-E) we evaluated the influence of hemoglobin on a very early, uncommitted progenitor cells, the Colony Forming Unit-Spleen (CFU-S). These cells have been shown to essentially give rise to erythroid, myeloid and lymphoid lineages and repopulate impaired bone marrow of lethally irradiated animals (van Zant, et. al., (1984) J. Exp. Med. 159: 679–685; Reincke, U., et al. (1985) Exp. Hematol. 13: 545–553). Repopulation of impaired bone marrow is indicative of the presence of multipotential stem cells that are represented by CFU-S. Spleen colonies were counted on day 8 following i.v. injection of 8.5 Gy-irradiated mice with $2 \times 10^5$ bone marrow cells from normal or AZT treated mice that had been further treated with either EPO, hemoglobin or combinations thereof, as described in Example 4. As seen in FIG. 11, hemoglobin at 5 and 10 mg/kg significantly increased the number of CFU-S that formed in mice that had been lethally irradiated and subsequently infused with bone marrow from the mice that received purified, recombinant hemoglobin in addition to AZT. The lower dose level, 0.5 mg of hemoglobin/kg of body weight appeared to work better than the higher dose of hemoglobin, suggesting a maximum effect at unexpectedly low doses. Without being bound by theory, the ability of hemoglobin to stimulate repopulation of the entire blood circulation indicates that low level hemoglobin administration works either directly on progenitor cells or indirectly to enhance hematopoiesis.

We claim:

1. A method for stimulating hematopoiesis in a mammal comprising administering to the mammal a therapeutically effective amount of purified hemoglobin.

2. A method according to claim 1 wherein the purified hemoglobin is a mutant hemoglobin.

3. A method according to claim 1 wherein the purified hemoglobin is a recombinantly produced hemoglobin.

4. A method according to claim 1 wherein the purified hemoglobin is selected from the group consisting of di-alpha hemoglobin, di-beta hemoglobin, octameric hemoglobin and multimeric hemoglobin.

5. A method according to claim 1 wherein the therapeutically effective amount of purified hemoglobin is from about 0.01 mg to 10000 mg/kg body weight.

6. A method according to claim 2 wherein the therapeutically effective amount of mutant hemoglobin is from about 0.01 mg to 10000 mg/kg body weight.

7. A method according to claim 3 wherein the therapeutically effective amount of recombinant hemoglobin is from about 0.01 mg to 10000 mg/kg body weight.

8. A method according to claim 3 wherein the therapeutically effective amount of recombinant mutant hemoglobin is from about 0.01 mg to 1000 mg/kg body weight.

9. A method according to claim 4 wherein the therapeutically effective amount of di-alpha hemoglobin, di-beta hemoglobin, octameric hemoglobin or multimeric hemoglobin is from about 0.01 mg to 1000 mg/kg body weight.

10. A method according to claim 1 wherein the therapeutically effective amount of purified hemoglobin is less than 1000 mg/kg body weight.

11. A method for alleviating cytopenia in a mammal comprising administration to the mammal of a cytopenia alleviating effective amount of purified hemoglobin.

12. The method according to claim 11 wherein the cytopenia is an anemia.

13. The method according to claim 12 wherein the anemia is the result of AZT treatment in a patient diagnosed with Human Immunodeficiency Virus (HIV).

14. A method for enhancing growth or differentiation of mammalian progenitor stem cells comprising administration to a purified culture of a mammalian stem cell population of a stem cell stimulatory effective amount of hemoglobin.

15. A method according to claim 14 wherein the mammalian progenitor stem cells are mammalian erythroid progenitor cells.

16. A method for stimulating hematopoiesis according to the method of claim 1, 11, 14 or 15 further comprising coadministration of one or more hematopoietic growth factor.

17. The method of claim 16 wherein said hematopoietic growth factor is selected from the group consisting of GM-CSF, M-CSF, G-CSF, SCF, EPO, IL-1, IL-2, IL-3, IL-4, IL-5, IL-6, IL-7, IL-8, IL-9, IL-10, IL-11, IL-12, IL-13, and platelet derived growth factor (PDGF).

18. A pharmaceutical composition useful for stimulating hematopoiesis according to claim 1 comprising:

about 0.1% to about 90% by weight to volume of substantially cell-free of hemoglobin,
0–50 mM Na bicarbonate,
0–150 mM NaCl,
0–100 mM alcohol sugar,
0–25 mM $CaCl_2$,
0–25 mM $MgCl_2$,
0–25 mM KCl, and
0–0.5% surfactant.

19. A pharmaceutical composition according to claim 18 wherein the final pH of the pharmaceutical composition is from about 7.0 to 7.8.

20. A pharmaceutical composition according to claim 19 wherein the alcohol sugar is selected from the group consisting of glucose, mannitol and sorbitol.

21. A pharmaceutical composition according to claim 18 wherein the pharmaceutical composition is:

about 0.1% to about 90% by weight to volume of substantially cell-free hemoglobin,
5 mM Na bicarbonate,
100 mM NaCl,
50 mannitol,
2 mM $CaCl_2$,
1 mM $MgCl_2$,
3 mM KCl,
0.03% Tween 80, and
pH of about 7.4.

22. A cell culture additive useful for enhancing growth or differentiation of mammalian progenitor stem cells according to claim 14 comprising:

about 0.1% to about 90% by weight to volume of substantially cell-free hemoglobin,
150 mM NaCl,
5 mM sodium phosphate, and
pH of about 7.4.

23. A cell culture additive useful for a method of enhancing growth and/or development of mammalian erythroid progenitor cells according to claim 15 comprising:

about 0.1% to about 90% by weight to volume of substantially cell-free hemoglobin,
150 mM NaCl,
5 mM sodium phosphate, and
pH of about 7.4.

24. The method of claim 17, wherein the hematopoietic growth factor is EPO.

* * * * *